US012588827B2

(12) United States Patent
Freeman et al.

(10) Patent No.: US 12,588,827 B2
(45) Date of Patent: Mar. 31, 2026

(54) DETERMINING DIFFERENT SLEEP STAGES IN A WEARABLE MEDICAL DEVICE PATIENT

(71) Applicant: ZOLL MEDICAL CORPORATION, Chelmsford, MA (US)

(72) Inventors: Gary A. Freeman, Waltham, MA (US); Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 691 days.

(21) Appl. No.: 17/907,650

(22) PCT Filed: Mar. 26, 2021

(86) PCT No.: PCT/US2021/024418
§ 371 (c)(1),
(2) Date: Sep. 28, 2022

(87) PCT Pub. No.: WO2021/202291
PCT Pub. Date: Oct. 7, 2021

(65) Prior Publication Data
US 2023/0218186 A1      Jul. 13, 2023

Related U.S. Application Data

(60) Provisional application No. 63/002,663, filed on Mar. 31, 2020.

(51) Int. Cl.
*A61N 1/39* (2006.01)
*A61B 5/0245* (2006.01)
(Continued)

(52) U.S. Cl.
CPC .......... *A61B 5/02455* (2013.01); *A61B 5/053* (2013.01); *A61N 1/3702* (2013.01); *A61N 1/3904* (2017.08); *A61B 2562/02* (2013.01)

(58) Field of Classification Search
CPC ... A61B 5/0205; A61B 5/02405; A61B 5/361; A61B 5/4812; A61B 5/7275;
(Continued)

(56) References Cited

U.S. PATENT DOCUMENTS 4,576,170 A 3/1986 Bradley et al.
4,580,572 A 4/1986 Granek
(Continued)

FOREIGN PATENT DOCUMENTS

CN 101489478 B 7/2012
CN 103037760 A 4/2013
(Continued)

OTHER PUBLICATIONS

International Search Report and Written Opinion for PCT Application No. PCT/US2021/024418 Date of Mailing: Mar. 26, 2021 (24 pages).

*Primary Examiner* — Allen Porter
(74) *Attorney, Agent, or Firm* — Finch & Maloney PLLC

(57) ABSTRACT

A patient monitoring device configured to monitor cardiac activity and sleep stage information of a patient is provided. The device includes a plurality of electrodes to acquire electrocardiogram (ECG) signals from the patient, at least one motion sensor configured to generate a motion signal based upon movement of the patient, and at least one processor. The processor is configured derive motion parameters from the motion signal, derive ECG parameters from the ECG signals, determine whether the patient is in an immobilized sleep stage or a non-immobilized sleep stage based upon the motion parameters and the ECG parameters, adjust one or more cardiac arrhythmia detection parameters such that the device operates in a first monitoring and treatment mode when the patient is in an immobilized sleep (Continued)

stage, and monitor the patient for the cardiac arrhythmia using the first monitoring and treatment mode.

16 Claims, 18 Drawing Sheets

(51) Int. Cl.
*A61B 5/053* (2021.01)
*A61N 1/37* (2006.01)

(58) Field of Classification Search
CPC .............. A61N 1/3625; A61N 1/36521; A61N 1/36578; A61N 1/36585; A61N 1/3702; A61N 1/3904
See application file for complete search history.

(56) References Cited

U.S. PATENT DOCUMENTS

| | | | |
|---|---|---|---|
| 4,928,690 A | 5/1990 | Heilman | |
| 5,741,306 A | 4/1998 | Glegyak | |
| 5,944,669 A | 8/1999 | Kaib | |
| 6,065,154 A | 5/2000 | Hulings et al. | |
| 6,374,138 B1 | 4/2002 | Owen et al. | |
| 6,681,003 B2 | 1/2004 | Linder et al. | |
| 8,140,154 B2 | 3/2012 | Donnelly et al. | |
| 8,406,842 B2 | 3/2013 | Kaib et al. | |
| 8,562,526 B2 | 10/2013 | Heneghan et al. | |
| 2002/0198462 A1* | 12/2002 | Begemann | A61B 5/02405 |
| | | | 600/519 |
| 2008/0312709 A1 | 12/2008 | Volpe et al. | |
| 2010/0298899 A1 | 11/2010 | Donnelly et al. | |
| 2011/0130800 A1* | 6/2011 | Weinstein | A61B 5/0507 |
| | | | 600/509 |
| 2011/0301479 A1* | 12/2011 | Ghanem | A61N 1/3925 |
| | | | 600/515 |
| 2011/0301513 A1 | 12/2011 | Freeman | |
| 2014/0277232 A1 | 9/2014 | Libbus et al. | |
| 2015/0224330 A1 | 8/2015 | Kaib et al. | |
| 2016/0175603 A1 | 6/2016 | Sheldon et al. | |
| 2017/0087371 A1 | 3/2017 | Freeman et al. | |
| 2017/0143977 A1 | 5/2017 | Kaib et al. | |
| 2018/0185662 A1 | 7/2018 | Foshee, Jr. et al. | |
| 2019/0143133 A9 | 5/2019 | Foshee, Jr. et al. | |
| 2020/0086078 A1* | 3/2020 | Poltorak | A61N 2/006 |

FOREIGN PATENT DOCUMENTS

| | | |
|---|---|---|
| CN | 110639113 A | 1/2020 |
| EP | 1859733 A1 | 11/2007 |
| EP | 1938862 A2 | 7/2008 |
| WO | 2019030746 A1 | 2/2019 |

* cited by examiner

500

502
RECEIVE AND MONITOR PATIENT INFORMATION

504
PATIENT ASLEEP?

NO

YES

506
IMMOBILIZED SLEEP?

NO

YES

508
MONITOR THE PATIENT IN A NON-IMMOBILIZED SLEEP MODE

510
DETERMINE UPDATED OPERATIONAL PARAMETERS

512
ADJUST ONE OR MORE OPERATIONAL PARAMETERS

514
MONITOR THE PATIENT IN AN IMMOBILIZED SLEEP MODE

506

600 —

602

MONITOR SLEEPING PATIENT

604

SLEEP STAGE TRANSITION?

NO

YES

606

UPDATE OPERATIONAL PARAMETERS

608

MONITOR PATIENT USING UPDATED SLEEP STAGE MONITORING MODE

700 —

900

1000

DETERMINING DIFFERENT SLEEP STAGES IN A WEARABLE MEDICAL DEVICE PATIENT

CROSS-REFERENCE TO RELATED APPLICATION

This application claims priority under 35 U.S.C. § 371 as a national stage application of PCT Application No. PCT/US2021/024418, titled "Determining Different Sleep Stages in a Wearable Medical Device Patient," filed Mar. 26, 2021, which claims under 35 U.S.C. § 119(e) to U.S. Provisional Application No. 63/002,663 titled "Determining Different Sleep Stages in a Wearable Medical Device Patient," filed Mar. 31, 2020, each of which is hereby incorporated herein by reference in its entirety.

BACKGROUND

The present disclosure is directed to monitoring a sleeping patient that is prescribed a wearable medical device.

Heart failure, if left untreated, can lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life. It is generally useful to monitor heart failure patients to assess heart failure symptoms early and provide interventional therapies as soon as possible.

Patients who are at risk, have been hospitalized for, or otherwise are suffering from, adverse heart conditions can be prescribed a wearable cardiac monitoring and/or treatment device. In addition to the wearable device, the patient can also be given a battery charger and a set of rechargeable batteries. As the wearable device is generally prescribed for continuous or near-continuous use (e.g., only to be removed when bathing), the patient wears the device during all daily activities such as walking, sitting, climbing stairs, resting or sleeping, and other similar daily activities.

When asleep, the patient's body undergoes physiological changes over the course of the sleep period. For example, the patient may be in a rapid eye movement (REM) sleep stage, a light sleep stage (non-REM), or one of different deep sleep stages characterized by reduced movement of the patient's body during the deep sleep stages (e.g., deep sleep graded from 1 through 3 or other predetermined gradations).

SUMMARY

In an example, a patient monitoring device configured to monitor cardiac activity and sleep stage information of a patient is provided. The patient monitoring device includes a plurality of electrodes configured to be coupled externally to a patient to acquire electrocardiogram (ECG) signals from the patient and provide a therapeutic shock to the patient in response to detection of a cardiac arrhythmia, at least one motion sensor configured to generate at least one motion signal based upon movement of the patient, and at least one processor operably coupled to the plurality of electrodes and the at least one motion sensor. The at least one processor is configured to receive the at least one motion signal from the at least one motion sensor and derive one or more motion parameters from the at least one motion signal, receive the ECG signals from the at least one electrode and derive one or more ECG parameters from the ECG signals, determine whether the patient is in an immobilized sleep stage or a non-immobilized sleep stage based upon analysis of the one or more motion parameters and the one or more ECG parameters, adjust one or more cardiac arrhythmia detection parameters such that the device operates in a first monitoring and treatment mode when the at least one processor determines that the patient is in an immobilized sleep stage, and monitor the patient for the cardiac arrhythmia using the first monitoring and treatment mode.

Implementations of the patient monitoring device can include one or more of the following features.

In the patient monitoring device, the at least one processor can be configured to determine whether the patient is in an immobilized sleep stage by being configured to monitor the ECG signals to determine whether heart rate deviation from a baseline resting heart rate for the patient exceeds a deviation threshold over a period of time, analyze the one or more motion parameters over the period of time, and determine if the patient is in an immobilized sleep stage based upon the heart rate deviation and analysis of the one or more motion parameters over the period of time. In some examples, the deviation threshold includes at least one of greater than 1% deviation from the baseline resting heart rate, greater than 2% deviation from the baseline resting heart rate, and greater than 5% deviation from the baseline resting heart rate. In some examples, the period of time can include at least one of five minutes, seven minutes, ten minutes, thirty minutes, forty-five minutes, and one hour.

In the patient monitoring device, the at least one processor can be configured to adjust the one or more cardiac arrhythmia detection parameters such that the device operates in a second monitoring and treatment mode and monitor the patient for the cardiac arrhythmia using the second monitoring and treatment mode. In some examples, the at least one processor is further configured to monitor the patient using the second monitoring and treatment mode, determine whether the patient has transitioned from the non-immobilized sleep stage to the immobilized sleep stage, and monitor the patient using the first monitoring and treatment mode when the at least one processor determines that the patient has transitioned from the non-immobilized sleep stage to the immobilized sleep stage.

In the patient monitoring device, the at least one processor can be configured to commence monitoring a physiological signal other than the ECG signals when the at least one processor determines that the patient is in an immobilized sleep stage. In some examples, the patient monitoring device can include a radio-frequency (RF) sensor, the physiological signal other than the ECG signals can include radio-RF-based physiological signals, and the at least one processor can be configured to determine at least one of heart wall movement information and thoracic fluid level information from the RF-based physiological signals. In some examples, the patient monitoring device can include a cardiovibrational sensor, the physiological signal other than the ECG signals can include one or more cardiovibrational signals of the patient, and the at least one processor can be configured to determine one or more electromechanical parameters of a heart of the patient based on the cardiovibrational signals.

In the patient monitoring device, the at least one processor can be configured to adjust one or more treatment parameters when the at least one processor determines that the patient is in an immobilized sleep stage. In some examples, the one or more treatment parameters can include one or more of a pacing pulse rate, a high-energy pacing pulse energy level, a low-energy pacing pulse level, a defibrillation shock energy level, and defibrillation shock timing information.

In the patient monitoring device, the at least one processor can be configured to adjust one or more alarm parameters when the at least one processor determines that the patient is in an immobilized sleep stage. In some examples, the one or more alarm parameters can include at least one of alarm type, alarm volume, alarm duration, and patient response time information.

In the patient monitoring device, the one or more motion parameters can include a rotational motion parameter that quantifies rotational motion of the patient as measured by the at least one motion sensor.

In the patient monitoring device, the immobilized sleep stage can include at least one of an N3 sleep stage, an N4 sleep stage, and an REM sleep stage.

In the patient monitoring device, the non-immobilized sleep stage can include at least one of consciousness, an N1 sleep stage, and an N2 sleep stage.

In the patient monitoring device, the one or more motion parameters can include one or more of patient respiration information, patient physical movement information, and patient body position information.

In the patient monitoring device, the at least one processor can be further configured to derive one or more additional motion parameters from one or more impedance-based measurements from the plurality of electrodes.

In the patient monitoring device, the one or more ECG parameters can include one or more of heart rate, heart rate variability, premature ventricular contraction (PVC) burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T wave variability, and ST segment changes.

In the patient monitoring device, the one or more cardiac arrhythmia detection parameters can include one or more of a ventricular tachycardia onset heart rate, a ventricular fibrillation onset heart rate, a bradycardia onset heart rate, a tachycardia onset heart rate, and an asystole onset threshold.

In the patient monitoring device, the at least one processor can be further configured to adjust at least one of a cardiac arrhythmia detection confidence level and a noise threshold when the at least one processor determines that the patient is in an immobilized sleep stage.

In the patient monitoring device, the at least one processor can be further configured to monitor a heart rate of the patient when the processor determines that the patient is in an immobilized sleep stage to derive patient heart rate information, compare the patient heart rate information and baseline resting heart rate for the patient, and adjust and/or verify the baseline resting heart rate based upon the comparing of the heart rate information and the baseline resting heart rate to determine an updated baseline resting heart rate for the patient.

In the patient monitoring device, the at least one processor can be further configured to, when the processor determines that the patient is in an immobilized sleep stage, determine at least one occurrence of a PVC from the ECG signals, upon occurrence of the PVC, monitor changes in the ECG signals to measure a cardiac response of a heart of the patient following the PVC, determine a heart rate turbulence value for the patient based upon the monitored changes in the electrical signal, and store the heart rate turbulence value on a computer-readable medium operably coupled to the at least one processor for analysis.

In another example, a second patient monitoring device configured to monitor cardiac activity and sleep stage information of a patient is provided. The second patient monitoring device includes a plurality of electrodes configured to be coupled externally to a patient to acquire ECG signals from the patient and provide a therapeutic shock to the patient in response to detection of a cardiac arrhythmia, at least one motion sensor configured to generate at least one motion signal based upon movement of the patient, and at least one processor operably coupled to the plurality of electrodes and the at least one motion sensor. The at least one processor is configured to receive the at least one motion signal from the at least one motion sensor and derive one or more motion parameters from the at least one motion signal, receive the ECG signals from the at least one electrode and derive one or more ECG parameters from the ECG signals, determine whether the patient is in an immobilized sleep stage or a non-immobilized sleep stage based upon analysis of the one or more motion parameters and the one or more ECG parameters, adjust one or more alarm parameters such that the device operates in a first alarm mode when the at least one processor determines that the patient is in an immobilized sleep stage, and alert the patient of the cardiac arrhythmia using the first alarm mode.

Implementations of the second patient monitoring device can include one or more of the following features.

In the second patient monitoring device, the at least one processor can be configured to determine whether the patient is in an immobilized sleep stage by being configured to monitor the ECG signals to determine whether heart rate deviation from a baseline resting heart rate for the patient exceeds a deviation threshold over a period of time, analyze the one or more motion parameters over the period of time, and determine if the patient is in an immobilized sleep stage based upon the heart rate deviation and analysis of the one or more motion parameters over the period of time. In some examples, the deviation threshold can include at least one of greater than 1% deviation from the baseline resting heart rate, greater than 2% deviation from the baseline resting heart rate, and greater than 5% deviation from the baseline resting heart rate. In some examples, the period of time can include at least one of five minutes, seven minutes, ten minutes, thirty minutes, forty-five minutes, and one hour.

In the second patient monitoring device, the at least one processor can be configured to adjust the one or more alarm parameters such that the device operates in a second alarm mode and alert the patient of the cardiac arrhythmia using the second alarm mode.

In the second patient monitoring device, the one or more alarm parameters can include at least one of alarm type, alarm volume, alarm duration, and patient response time information.

In the second patient monitoring device, the one or more motion parameters can include a rotational motion parameter that quantifies rotational motion of the patient as measured by the at least one motion sensor.

In the second patient monitoring device, the immobilized sleep stage can include at least one of an N3 sleep stage, an N4 sleep stage, and an REM sleep stage.

In the second patient monitoring device, the non-immobilized sleep stage can include at least one of consciousness, an N1 sleep stage, and an N2 sleep stage.

In the second patient monitoring device, the one or more motion parameters can include one or more of patient respiration information, patient physical movement information, and patient body position information.

In the second patient monitoring device, the at least one processor can be further configured to derive one or more additional motion parameters from one or more impedance-based measurements from the plurality of electrodes.

In the second patient monitoring device, the one or more ECG parameters can include one or more of heart rate, heart rate variability, premature ventricular contraction (PVC) burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T wave variability, and ST segment changes.

In another example, a third patient monitoring device configured to monitor cardiac activity and sleep stage information of a patient is provided. The third patient monitoring device includes a plurality of electrodes configured to be coupled externally to a patient to acquire electrocardiogram (ECG) signals from the patient and provide a therapeutic shock to the patient in response to detection of a cardiac arrhythmia, at least one physiological sensor configured to be coupled externally to the patient to acquire a physiological signal other than the ECG signals, at least one motion sensor configured to generate at least one motion signal based upon movement of the patient, and at least one processor operably coupled to the plurality of electrodes and the at least one motion sensor. The at least one processor is configured to receive the at least one motion signal from the at least one motion sensor and derive one or more motion parameters from the at least one motion signal, receive the ECG signals from the at least one electrode and derive one or more ECG parameters from the ECG signals, determine whether the patient is in an immobilized sleep stage or a non-immobilized sleep stage based upon analysis of the one or more motion parameters and the one or more ECG parameters, commence monitoring the physiological signal other than the ECG signals when the at least one processor determines that the patient is in an immobilized sleep stage, and determine at least one additional physiological parameter of the patient based upon analysis of the physiological signal other than the ECG signals.

Implementations of the third patient monitoring device can include one or more of the following features.

In the third patient monitoring device, the at least one physiological sensor can include a radio-frequency (RF) sensor and the physiological signal other than the ECG signals can include radio-RF-based physiological signals. In some examples, the at least one additional physiological parameter can include at least one of heart wall movement information and thoracic fluid level information from the RF-based physiological signals.

In the third patient monitoring device, the at least one physiological sensor can include a cardiovibrational sensor and the physiological signal other than the ECG signals can include one or more cardiovibrational signals of the patient. In some examples, the at least one additional physiological parameter can include one or more electromechanical parameters of a heart of the patient based on the cardiovibrational signals.

In the third patient monitoring device, the at least one processor can be configured to determine whether the patient is in an immobilized sleep stage by being configured to monitor the ECG signals to determine whether heart rate deviation from a baseline resting heart rate for the patient exceeds a deviation threshold over a period of time, analyze the one or more motion parameters over the period of time, and determine if the patient is in an immobilized sleep stage based upon the heart rate deviation and analysis of the one or more motion parameters over the period of time. In some examples, the deviation threshold can include at least one of greater than 1% deviation from the baseline resting heart rate, greater than 2% deviation from the baseline resting heart rate, and greater than 5% deviation from the baseline resting heart rate. In some examples, the period of time can include at least one of five minutes, seven minutes, ten minutes, thirty minutes, forty-five minutes, and one hour.

In the third patient monitoring device, the one or more motion parameters can include a rotational motion parameter that quantifies rotational motion of the patient as measured by the at least one motion sensor.

In the third patient monitoring device, the immobilized sleep stage can include at least one of an N3 sleep stage, an N4 sleep stage, and an REM sleep stage.

In the third patient monitoring device, the non-immobilized sleep stage can include at least one of consciousness, an N1 sleep stage, and an N2 sleep stage.

In the third patient monitoring device, the one or more motion parameters can include one or more of patient respiration information, patient physical movement information, and patient body position information.

In the third patient monitoring device, the at least one processor can be further configured to derive one or more additional motion parameters from one or more impedance-based measurements from the plurality of electrodes.

In the third patient monitoring device, the one or more ECG parameters can include one or more of heart rate, heart rate variability, premature ventricular contraction (PVC) burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T wave variability, and ST segment changes.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1A:
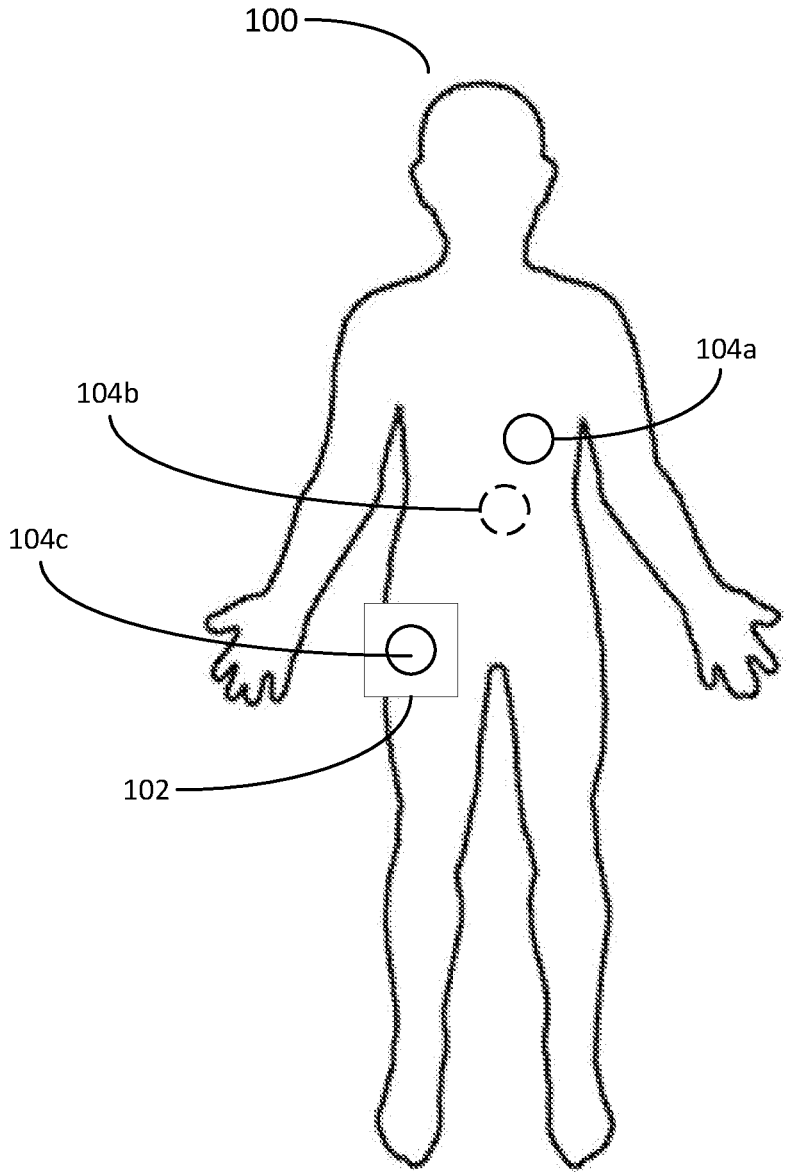
FIGS. 1A and 1B illustrate sample sensor arrangements for a patient, in accordance with an example of the present disclosure.

Wearable medical devices, such as cardiac event monitoring and/or treatment devices, are used in clinical or outpatient settings to monitor and/or record various ECG and other physiological signals of a patient. These ECG and other physiological signals can be used to monitor for arrhythmias, and, in example devices described herein, provide treatment such as a defibrillation or pacing shocks in the event of life-threatening arrhythmias. An example cardiac monitoring and treatment device that can implement the sleep stage features and/or processes described herein includes a wearable defibrillator, also called wearable cardioverter defibrillator (WCDs). Another example cardiac monitoring and treatment device that can implement the sleep stage features and/or processes described herein include a hospital wearable defibrillator (HWD).

During continuous monitoring of a patient for arrhythmia conditions (e.g., over the course of 24 hours a day, 7 days a week), the patient may regularly enter into sleep periods often characterized as periods of time with reduced or no physical movement. During such sleep periods, wearable medical devices described herein can be automatically or manually caused to change operation from a non-sleep period mode to a sleep period mode. For example, the devices can automatically enter the sleep period mode based on detection of certain parameters such as the patient movement falling below a certain patient motion threshold and/or heart rate falling below a predetermined heart rate threshold. Additionally or alternatively, the devices may automatically enter the sleep period mode based on the time of the day, e.g., a pre-set time such as 2200 hours (10 PM). In implementations, the certain patient motion threshold, predetermined heart rate threshold, and the time of day can be set via prescriber-controllable parameters. For example, default values for such parameters can be set, and a prescriber can change the defaults to other desired values. Still additionally or alternatively, the devices can enter the sleep period mode based on user input, e.g., a patient indicating via a user interface parameter that the patient is about to sleep. On receiving such user input, the devices can enter the sleep period mode after a predetermined delay, e.g., a default value of around 30 minutes that can be prescriber controlled to a different other desired value.

In examples, the devices can be configured to ignore brief periods of sleep such as nap periods. For example, the devices can be configured to enter the sleep period mode after a predetermined delay (e.g., a default value of around 45 minutes) that can be prescriber controlled to a desired value (e.g., set in a range from 15 minutes to 90 minutes). The predetermined delay period can be measured from when the device determines that the patient motion has fallen below a certain patient motion threshold and/or a predetermined heart rate threshold.

The sleep period mode can have additional modes based upon what stage of sleep the patient is in. For example, when a patient is in an immobilized sleep stage, the wearable medical device can monitor the patient in an immobilized sleep stage mode that includes one or more operational parameters that have been adjusted to accommodate the immobilized sleep stage of the patient. In certain examples, when a patient is in a non-immobilized sleep stage, the wearable medical device can monitor the patient in a non-immobilized sleep stage mode.

The devices implementing the sleep stage monitoring features and/or processes described herein provide advantages and benefits. For example, implementations described herein help with better diagnosis and/or and improve arrhythmia monitoring and treatment of a sleeping patient than implementations that do not incorporate such features and/or processes. In one example, implementations herein can better monitor for certain arrhythmias such as bradycardia by discriminating such a condition from a low resting heart rate condition when the patient is in an immobilized sleep stage. Such implementations can improve wearable defibrillators by properly monitoring and treating patients for arrhythmias that they are actually experiencing. Further, implementations herein can help reduce false alarms during periods when the patient is asleep.

In another example advantage or benefit, the implementations herein can help reduce inappropriate shock treatments by better adapting the alarm scheme (e.g., audio and/or vibrational alarm) to the patient's stage of sleep. In some examples, if the patient is in a deep sleep stage, the patient may not perceive an alarm or other warnings produced by the device before an unwarranted treatment. It is therefore advantageous to determine a sleep stage of a sleeping patient and determine what actions, if any, may be taken to adjust one or more operational parameters of a wearable medical device without impacting monitoring and/or treatment of the patient if the patient is experiencing an arrhythmia.

To address these and other aspects that enhance execution of arrhythmia monitoring and treatment of a sleeping patient, systems and processes configured to classify sleep stage information for a patient and modify one or more operational parameters of a wearable medical device based upon the sleep stage information are provided. For example, a WCD can include multiple sleep stage-based monitoring and treatment modes that can be selected by a processor based upon what sleep stage a patient is currently in. For example, the multiple monitoring and treatment modes can include a default monitoring and treatment mode (non-sleep period mode) for when the patient is awake. Sleep period modes can further include a non-immobilized sleep stage mode for when a patient is in a non-immobilized sleep stage as well as an immobilized sleep stage mode for when a patient is in an immobilized sleep stage as described herein.

For example, a patient monitoring device configured to monitor cardiac activity and sleep stage information of a patient can include multiple electrodes configured to be coupled externally to the patient and to acquire ECG signals from the patient and provide a therapeutic shock to the patient in response to detection of a cardiac arrhythmia as well as a motion sensor configured to generate a motion signal based upon movement of the patient. The device can further include a processor operably coupled to the plurality of electrodes and the at least one motion sensor. In some examples, the processor can be configured to receive the motion signal from and derive one or more motion parameters from the at least one motion signal. The processor can further receive the ECG signals from the electrodes and derive one or more ECG parameters from the ECG signals. Based upon the one or more motion parameters and the one or more ECG parameters, the processor can determine whether the patient is in an immobilized sleep stage or a non-immobilized sleep stage. If the patient is in an immobilized sleep stage, the processor can adjust one or more cardiac arrhythmia detection parameters such that the patient monitoring device operates in a first monitoring and treatment mode and monitor the patient for the cardiac arrhythmia using the first monitoring and treatment mode. In some examples, if the patient is in a non-immobilized sleep stage, the processor can be configured to operate the patient monitoring device in a second monitoring and treatment mode.

In a similar example, the processor can be configured to update one or more operational parameters if the patient is in an immobilized sleep stage. For example, the processor can be configured to adjust one or more alarm parameters when the patient is in an immobilized sleep stage. In certain implementations, the one or more alarm parameters can include alarm type, alarm volume, alarm duration, and patient response time to an alarm as described herein.

In another example, a patient monitoring device can be configured to perform additional patient monitoring when a patient is in a particular sleep stage. For example, a patient monitoring device such as that described above can further include an additional physiological sensor coupled externally to the patient and configured to acquire a physiological signal other than an ECG signal for analysis. In certain implementations, the additional physiological sensor can include an RF sensor that is configured to acquire RF-based physiological signals for the patient. In some examples, the processor as described above can be configured to commence monitoring of the physiological signal other than the ECG signals when the patient is in an immobilized sleep stage and determine one or more non-ECG physiological parameters for the patient based upon analysis of the non-ECG physiological signal.

These examples, and various other similar examples of benefits and advantages of the techniques, processes, and approaches as provided herein, are described in additional detail below.

A patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed such specialized cardiac monitoring and treatment devices. The sleep stage monitoring features and/or processes described herein in reference to a WCD can be applied in a substantially similar manner in an HWD.

The various monitoring processes as described herein are implemented in either the WCD or HWD device itself or in data processing devices such as remote server systems that are in communication with or otherwise associated with the WCD or HWD. For example, some or all steps of the processes described herein can be executed on a server and one or more of the results of such steps can be implemented by the device.

In one example, a WCD as described herein can include the LifeVest® Wearable Cardioverter Defibrillator from ZOLL Medical Corporation (Chelmsford, MA). As described in further detail below, such a device includes a garment that is configured to be worn about the torso of the patient. The garment can be configured to house various components such as ECG sensing electrodes, therapy electrodes, one or more accelerometers configured to measure motion data for the patient, one or more audio and/or vibrational sensors configured to record vibrational signals such as cardiovibrational signals for the patient, and one or more radio-frequency (RF) sensors configured to measure RF-based physiological signals. The components in the garment can be operably connected to a monitoring device disposed within a separate housing (e.g., that may be waterproof and/or protected from ingress of dirt or other physical particles) that is configured to receive and process signals from the ECG sensing electrodes to determine a patient's cardiac condition and, if necessary, provide treatment to the patient using the therapy electrodes.

An HWD can include two or more adhesive ECG sensing and/or therapy electrodes that are coupled via cables to a monitoring device disposed within a housing similar to one described above for a WCD.

The monitoring device of the WCD described herein is configured to determine if the patient is currently in an immobilized sleep stage and adjust one or more operational parameters of the monitoring device accordingly.

Figure 1B:
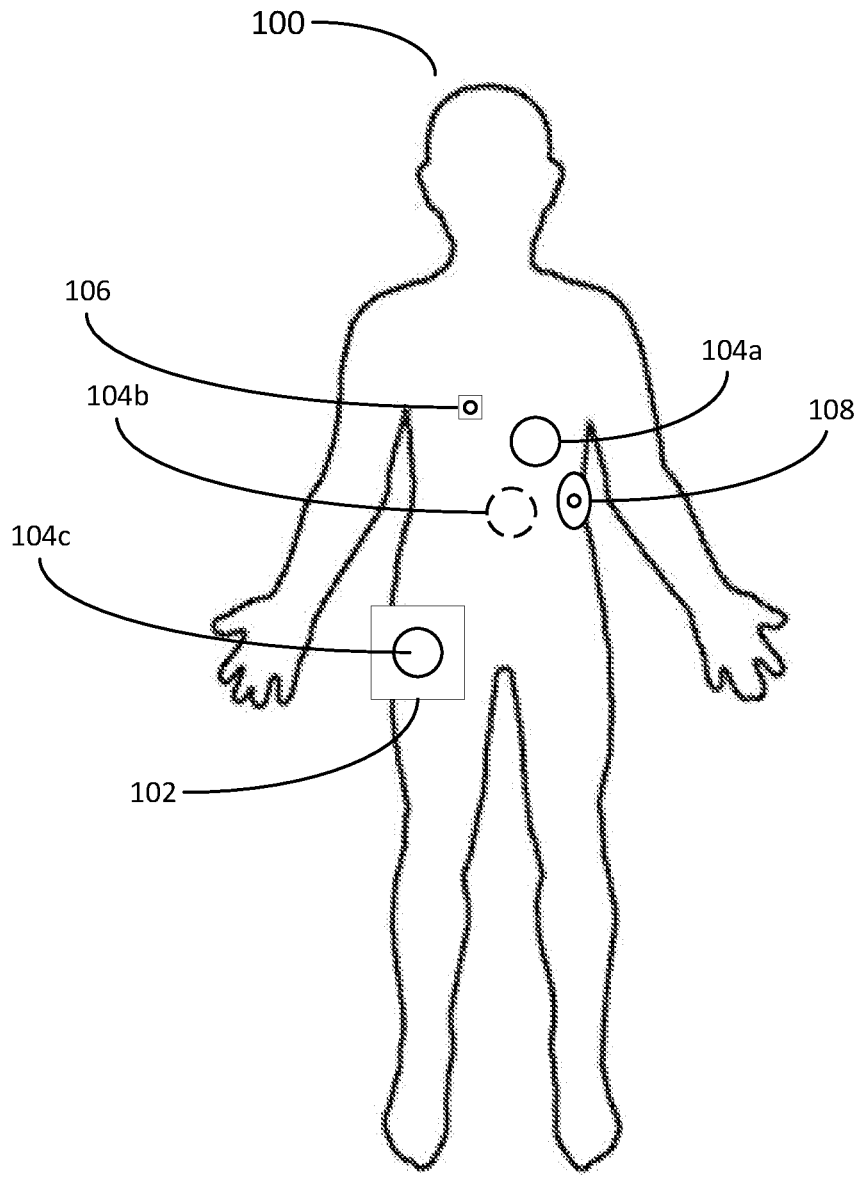

FIGS. 1A and 1B illustrate various examples of a patient 100 wearing one or more sensors such as accelerometers, audio and/or vibrational sensors, RF sensors, stretch or pressure sensors embedded in the garment, and other similar sensors as described herein. It should be noted that accelerometers are described herein as examples of motion sensors for illustrative purposes only. In certain implementations, additional motion sensors such as gyroscopes, magnetic sensors, pressure-based motion sensors, and other similar motion sensors can be used.

As shown in FIG. 1A, a patient can be prescribed an ambulatory medical device such as a WCD (or, for an in-patient hospital, an HWD). The WCD can include a controller 102 that is operably connected to one or more sensing electrodes and therapy electrodes. Additional details of one example of the controller 102 can be found in the discussion of FIG. 3 below.

The WCD can also include one or more accelerometers or other motion sensors. As shown in FIG. 1A, the WCD can include three accelerometers 104a, 104b, and 104c (collectively referred to as accelerometers 104) positioned at various places on the body of patient 100. For example, accelerometer 104a can be positioned on the front of chest of the patient 100, the accelerometer 104b can be positioned on the back of the patient, and the accelerometer 104c can be integrated into the controller 102. Each of the accelerometers 104 can be configured to measure movement associated with the patient 100 and to output an electrical signal indicating a direction and magnitude of the movement of the patient.

It should be noted that the number and arrangement of the accelerometers 104 as shown in FIG. 1 is by way of example only. In certain implementations, the number and position of the accelerometers 104 can vary. Additionally, when included in a device such as a WCD, one or more of the accelerometers 104 can be integrated into components of the WCD. For example, as noted above, the accelerometer 104c can be integrated into a controller 102 of the WCD. Similarly, one or more of accelerometers 104a and 104b can be integrated into one or more components of a WCD. For example, the front accelerometer 104a can be integrated into, for example, a therapy electrode operably connected to the controller 102 and configured to provide a therapeutic shock to patient 100. In some implementations, the accelerometer 104a can be integrated into a sensing electrode configured to measure electrical signals produced by patient 100 and indicative of cardiac activity of the patient. Similarly, accelerometer 104b can be integrated into one or more components of a WCD such as a connection node, a sensing electrode, a therapy electrode, and other similar components of a WCD as described herein. Alternatively or additionally, the one or more accelerometers 104 can be distinct components of the WCD.

In HWD implementations, the accelerometers can be integrated into one or more of the adhesive ECG sensing and/or therapy electrode patches. For example, a first accelerometer can be integrated into a first adhesive ECG sensing and/or therapy electrode patch and a second accelerometer can be integrated into a second adhesive ECG sensing and/or therapy electrode patch. Additional accelerometers can be disposed within a controller (similar to controller 102 of a WCD) associated with the HWD.

In addition to accelerometers associated with a WCD as described above in regard to FIG. 1A, a patient such as patient 100 can also wear additional sensors. As shown in FIG. 1B, patient 100 can wear a vibrational sensor 106 that is configured to record bio-vibrational signals of the patient. For example, the vibrational sensor 106 can be configured to detect a patient's vibrations associated with, for example, heart and lung activity. In certain implementations, the vibrational sensor 106 can be configured to detect cardiovibrational values including any one or all of S1, S2, S3, and S4. From these cardiovibrational values, certain heart vibration metrics or combinational metrics may be calculated, including any one or more of electromechanical activation time (EMAT), left ventricular systolic time (LVST), or percentage of left ventricular systolic time (% LVST). In some examples, the vibrational sensor 106 can include a vibration sensor configured to detect vibrations from a subject's cardiac system and provide an output signal responsive to the detected cardiovibrational values. The vibrational sensor 106 can also include a multi-channel accelerometer, for example, a three-channel accelerometer configured to sense movement in each of three orthogonal axes such that patient movement/body position can be detected and correlated to detected cardiovibrational values. The vibrational sensor 106 can transmit information descriptive of the cardiovibrational values to, for example, a sensor interface for subsequent analysis as described below.

Additionally, the patient 100 can wear an RF sensor 108. For example, the RF sensor can be configured to use RF-based techniques to assess fluid levels and accumulation in a patient's body tissue. For example, the RF sensor 108 can be configured to measure fluid content in the lungs, typically for diagnosis and follow-up of pulmonary edema or lung congestion in heart failure patients. Similarly, the RF sensor can be configured to measure thoracic fluid content for a patient. In certain implementations, the RF sensor 108 can include one or more antennas configured to direct radio frequency waves through a patient's tissue and measure output radio frequency signals in response to the waves that have passed through the tissue. In certain implementations, the output radio frequency signals include parameters indicative of a fluid level in the patient's tissue. The RF sensor 108 can transmit information descriptive of the tissue fluid levels to a sensor interface for subsequent analysis as described below.

It should be noted that the placement and number of sensors as shown in FIGS. 1A and 1B are shown by way of example only. In actual implementation of the patient sleep stage determination techniques as described herein, the number and position of the sensors can vary based upon the type of patient monitoring to be performed, the patient's typical sleeping habits, the patient's typical sleeping position and body orientation during sleep, and other various factors.

Figure 2:
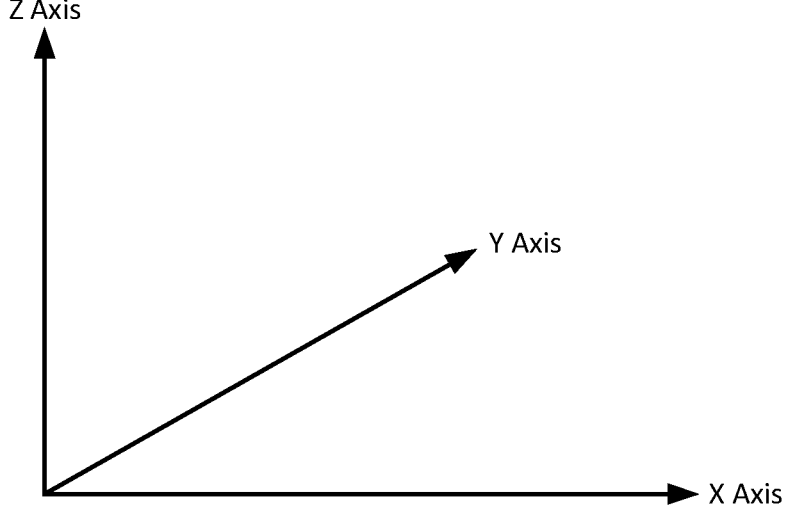
FIG. 2 illustrates the output of a sample accelerometer, in accordance with an example of the present disclosure.
Figure 2:
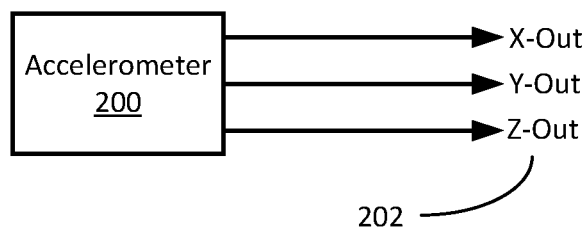

To properly acquire and output a signal indicative of a patient's movement when sleeping, an accelerometer such as those described above can be configured to output one or more output signals indicative of any detected movement or motion. For example, as shown in FIG. 2, an accelerometer 200 can be configured to measure movement in three axes: the x-axis, the y-axis, and the z-axis. Depending upon the orientation of the accelerometer 200 and the output configuration of the accelerometer, the individual axes can define movement of the accelerometer in a specific direction.

Additionally, as shown in FIG. 2, the accelerometer 200 can be configured to provide one or more outputs 202. In this example, the outputs 202 can include an X-out (i.e., a signal indicative of measured movement along the x-axis), a Y-out (i.e., a signal indicative of measured movement along the y-axis), and a Z-out (i.e., a signal indicative of measured movement along the z-axis).

In some implementations, an accelerometer such as accelerometer 200 can be configured to output an electrical signal on each output 202 having one or more controlled characteristics such as voltage. For example, the accelerometer 200 can be configured to output a signal on each output 202 between 0 and 5 volts. In some examples, the output voltage on each output 202 can be directly proportional to measured motion on the corresponding axis. For example, if the accelerometer 200 is configured to measure movement of acceleration as a measure of gravitational forces, the accelerometer can be configured to measure a specific range of g-forces such as −5 g to +5 g. In such an example, the output voltage on each output 202 can be directly proportional to the measured g-force on each axis. For example, if no g-forces are measured (i.e., the accelerometer 200 is at rest), each output signal 202 can be measured at 2.5 volts. If a movement having a positive g-force along an axis is measured, the voltage on the corresponding output 202 can increase. Conversely, if a movement having a negative g-force along an axis is measure, the voltage on the corresponding output 202 can decrease. Based upon these outputs 202, a processor such as those described herein can determine one or more motion parameters for a patient to be used when determining whether the patient is in an immobilized sleep stage or a non-immobilized sleep stage. Such details are provided in additional detail below.

Table 1 below shows sample voltage output levels for an accelerometer configured to measure between −5 g and +5 g and output a signal between 0 and 5 volts.

TABLE 1

| Measured G-Force | Output Voltage |
|---|---|
| −5 g | 0 volts |
| −4 g | 0.5 volts |
| −3 g | 1.0 volts |
| −2 g | 1.5 volts |
| −1 g | 2.0 volts |
| 0 g | 2.5 volts |
| 1 g | 3.0 volts |
| 2 g | 3.5 volts |
| 3 g | 4.0 volts |
| 4 g | 4.5 volts |
| 5 g | 5.0 volts |

It should be noted that sample g-force and voltage ranges as described above and shown in Table 1 are provided by way of example only for illustrative purposes. Depending upon the design and capabilities of the accelerometers used, the g-force ranges measured, and the corresponding output voltages, can vary accordingly.

Figure 3:
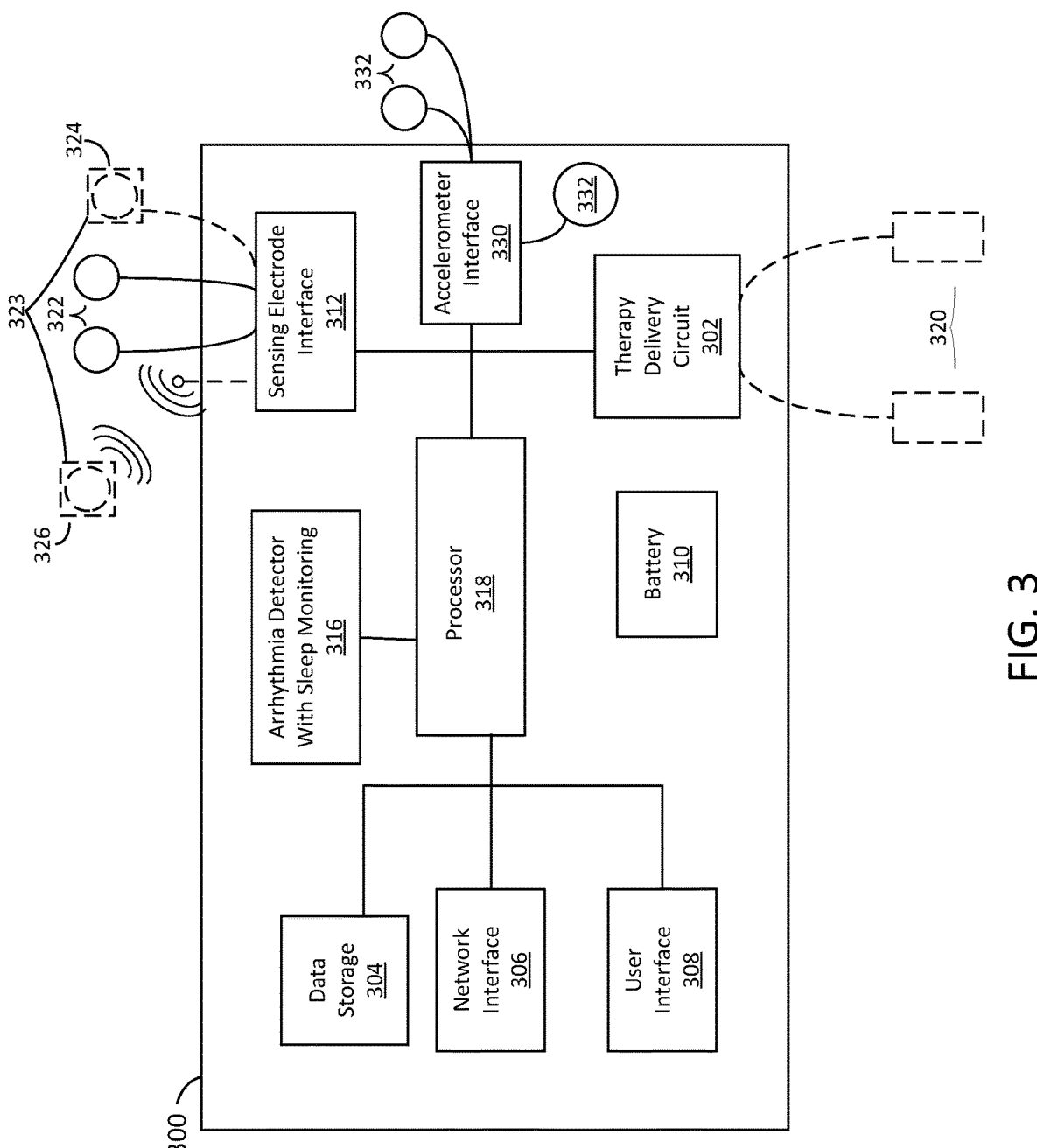
FIG. 3 illustrates a schematic view of a sample controller for a wearable medical device, in accordance with an example of the present disclosure.

FIG. 3 illustrates an example component-level view of the medical device controller 300 included in, for example, a wearable medical device such as a WCD or an HWD as described herein. The medical device controller 300 is one example of the controller 102 shown in FIGS. 1A and 1B and described above. As shown in FIG. 3, the medical device controller 300 can include a housing 301 configured to house a therapy delivery circuitry 302 configured to provide one or more therapeutic shocks to the patient via at least two therapy electrodes 320, a data storage 304, a network interface 306, a user interface 308, at least one rechargeable battery 310 (e.g., within a battery chamber configured for such purpose), a sensor interface 312 (e.g., to interface with both ECG sensing electrodes 322 and non-ECG physiological sensors 323 such as vibrational sensors (e.g., vibrational sensor 106), lung fluid sensors (e.g., RF sensor 108), infra-red and near-infrared-based pulse oxygen sensor, blood pressure sensors, among others), a cardiac event detector 316, and least one processor 318.

In some examples, the patient monitoring medical device can include a medical device controller 300 that includes like components as those described above but does not include the therapy delivery circuitry 302 and the therapy electrodes 320 (shown in dotted lines). That is, in certain implementations, the medical device can include only ECG monitoring components and not provide therapy to the patient. In such implementations, the construction of the patient monitoring medical device is similar in many respects as the medical device controller 300 but need not include the therapy delivery circuitry 302 and associated therapy electrodes 320.

As further shown in FIG. 3, the controller 300 can further include an accelerometer interface 330 and a set of accelerometers 332. The accelerometer interface 330 can be operably coupled to each of the accelerometers 332 and configured to receive one or more outputs from the accelerometers. The accelerometer interface 330 can be further configured to condition the output signals by, for example, converting analog accelerometer signals to digital signals (if using an analog accelerometer), filtering the output signals, combining the output signals into a combined directional signal (e.g., combining each x-axis signal into a composite x-axis signal, combining each y-axis signal into a composite y-axis signal, and combining each z-axis signal into a composite z-axis signal). In some examples, the accelerometer interface 330 can be configured to filter the signals using a high-pass or band-pass filter to isolate the acceleration of the patient due to movement from the component of the acceleration due to gravity.

Additionally, the accelerometer interface 330 can configure the output for further processing. For example, the accelerometer interface 330 can be configured to arrange the output of an individual accelerometer 332 as a vector expressing the acceleration components of the x-axis, the y-axis, and the z-axis as received from each accelerometer. The accelerometer interface 330 can be operably coupled to the processor 318 and configured to transfer the output signals from the accelerometers 332 to the processor for further processing and analysis.

As described above, one or more of the accelerometers 332 can be integrated into one or more components of a medical device. For example, as shown in FIG. 3, an accelerometer 332 can be integrated into the controller 300. In some examples, an accelerometer 332 can be integrated into one or more of a therapy electrode 320, a sensing electrode 322, a physiological sensor 323, and into other components of a medical device. When controller 300 is included in an HWD, an accelerometer can be integrated into an adhesive ECG sensing and/or therapy electrode patch.

As noted above, when a patient is sleeping, the cardiac activity and other similar physiological functions of the patient may change based upon what sleep stage the patient is in. Additionally, if the patient is in an immobilized sleep stage, additional monitoring and/or treatment functionality can be enabled while the patient remains in the immobilized sleep stage. In such an example, a medical device controller as described herein can be configured to monitor for motion information from, for example, an accelerometer interface as described above, the motion information indicative of movement of the patient. The medical device controller can analyze the motion information and derive one or more motion parameters. The medical device controller can further monitor for ECG signals from one or more sensing electrodes and derive one or more ECG parameters from the ECG signals. Based upon the motion parameters and the ECG parameters, the medical device controller can determine whether a patient is in an immobilized sleep stage or a non-immobilized sleep stage and adjust the monitoring and/or treatment of the patient accordingly.

Figure 4:
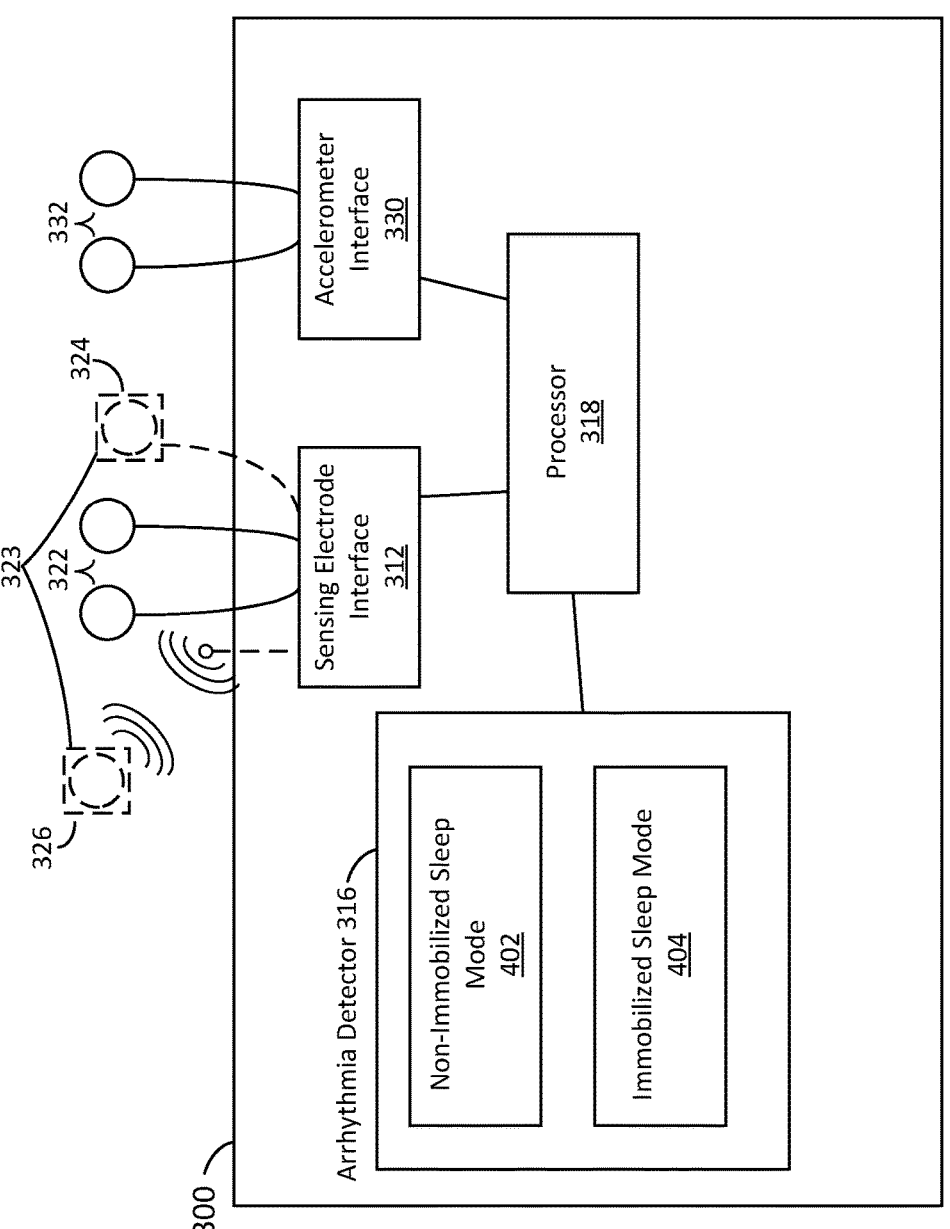
FIG. 4 illustrates a sample controller having multiple sleep stage modes for operation, in accordance with an example of the present disclosure.

For example, as shown in FIG. 4, the arrhythmia detector 316 of medical device controller 300 can include multiple monitoring and/or treatment modes for monitoring and/or treating a sleeping patient. As shown in FIG. 4, the arrhythmia detector 316 can include a non-immobilized sleep mode 402. If the processor 318 has derived motion parameters and/or ECG parameters that are associated with a non-immobilized sleep stage, the processor can switch to the non-immobilized sleep mode 402 for monitoring and treating the patient. As further shown in FIG. 4, the arrhythmia detector 316 can also include an immobilized sleep mode 404. If the processor 318 has derived motion parameters and/or ECG parameters that are associated with an immobilized sleep stage, the processor can switch to the immobilized sleep mode 404 for monitoring and treating the patient. More specific details of determining a patient sleep stage and switching a monitoring and/or treatment mode is described below in the discussion of FIGS. 5A and 5B.

Figure 5A:
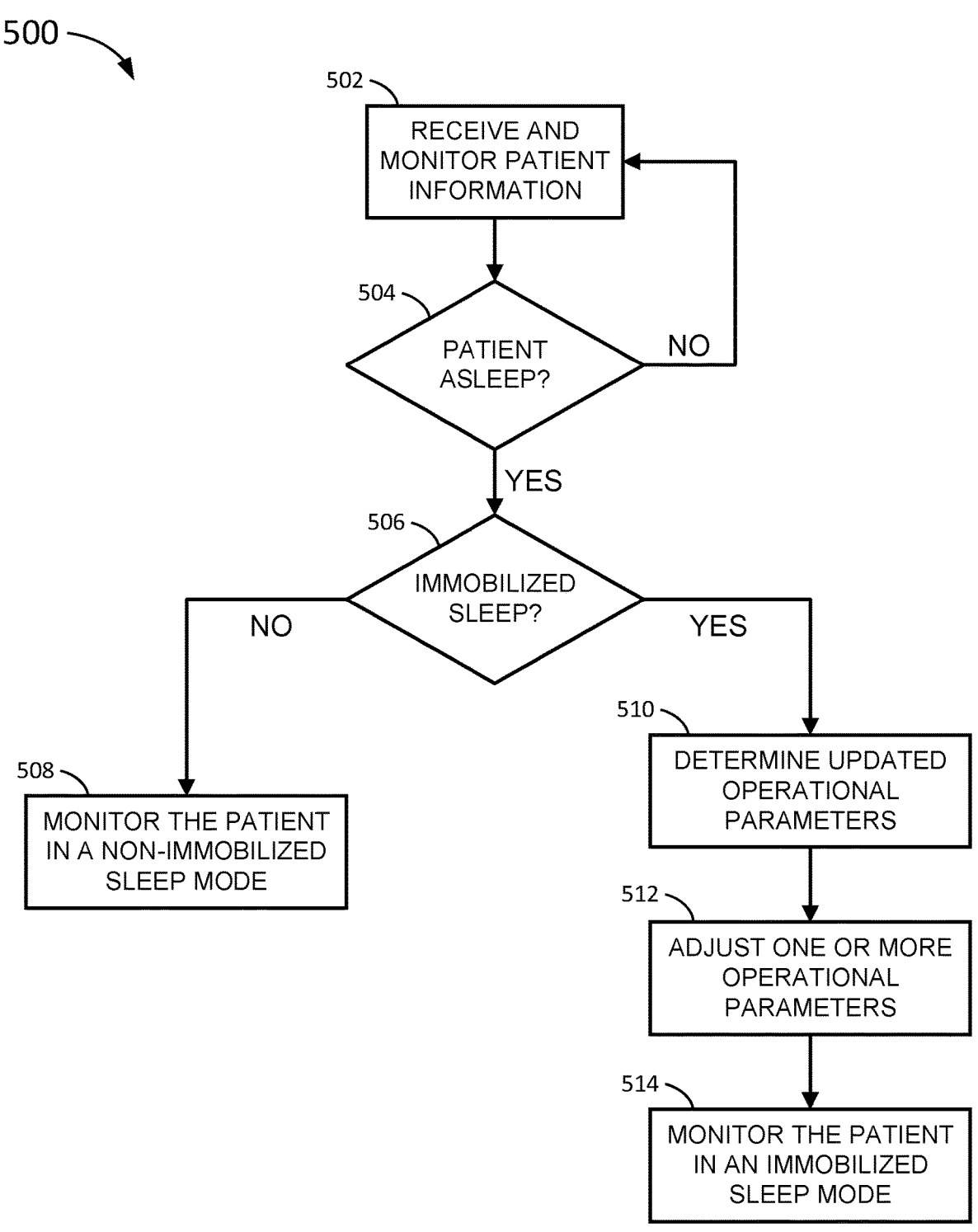
FIG. 5A illustrates a process flow for determining which sleep stage a patient is in, in accordance with an example of the present disclosure.

FIG. 5A illustrates a sample process 500 for determining what sleep stage a patient is in and adjusting monitoring and/or treatment of the patient accordingly. A processor such as processor 318 of medical device controller 300 as described above, can be configured to receive 502 and monitor patient information. For example, as described herein, the patient information can include patient motion information, patient ECG information, and other similar patient information such as patient respiratory information. Based upon this information, the processor can determine 504 whether the patient is asleep. For example, the processor can analyze the patient motion information to determine if the patient's movements have reduced. The processor can further analyze the patient's ECG information to determine if the patient's heart rate has reduced as well as analyze the patient's respiratory information to determine if the patient's breathing has slowed. In certain implementations, the processor can also consider additional data such as current time and historic sleep pattern information for the patient to determine if the patient is asleep.

Based upon this analysis, the processor can determine 504 whether the patient is asleep. If the processor determines 504 that the patient is not asleep, the processor can continue to receive 502 and monitor the patient's information. If the processor does determine 504 that the patient is asleep, the processor can further determine 506 whether the patient is in an immobilized sleep stage. Additional detail about determining whether the patient is asleep is provided in the discussion of FIG. 5B below. Similarly, additional detail about determining whether the patient is in an immobilized sleep stage is provided in the discussion of FIG. 5C below.

As further shown in FIG. 5A, if the processor does not determine that the patient is in an immobilized sleep stage, the processor can monitor 508 the patient using a non-immobilized sleep mode as described herein. Conversely, if the processor does determine 506 that the patient is in an immobilized sleep stage, the processor can determine 510 one or more updated operational parameters for the wearable medical device. For example, a patient's physician can provide updated operational parameters for the patient's wearable medical device based upon historic patient information and/or changes in the patient's treatment plan. The physician can enter the updated operational parameters into, for example, a physician's online portal and the updated operational parameters can be stored on a remote server or other similar remote computing device. In certain implementations, the updated operational parameters can include updated operational parameters for monitoring the patient when the patient is in an immobilized sleep stage. The processor can connect to the remote server to access the updated operational parameters. The processor can then determine 510 the updated operational parameters for monitoring the patient when the patient is in an immobilized sleep stage. Based upon the updated operational parameters, the processor can adjust 512 one or more operational parameters of the wearable medical device and monitor 514 the patient in an immobilized sleep mode as described herein.

It should be noted that, in certain implementations, the processor can determine 510 that the wearable medical device is already operating under the most recently updated set of operational parameters. In such an example, the processor can adjust 512 the operational parameters for monitoring the patient in an immobilized sleep stage based upon the existing operational parameters. Additionally, as noted below, the processor can be further configured to automatically adjust one or more operational parameters for monitoring a patient in an immobilized sleep stage based upon historical patient activity and monitored and/or observed occurrences associated with the patient.

In certain implementations, adjusting 512 the one or more operational parameters of the wearable medical device can include adjusting treatment parameters, adjusting alarm parameters, adjusting cardiac arrhythmia detection parameters, adjusting an arrhythmia detection confidence level, adjusting a noise threshold, and other similar operational parameters.

In some examples, adjusting the treatment parameters can include adjusting one or more of a pacing pulse rate, a high-energy pacing pulse energy level, a low-energy pacing pulse level, a defibrillation shock energy level, and defibrillation shock timing information. In some examples, adjusting the alarm parameters can include adjusting one or more of alarm type (e.g., tactile, audio, visual, a combination thereof), alarm volume, alarm duration, and patient response time information. For example, when a patient is in an immobilized sleep stage, the alarm type can include vibration followed by an audible alarm at a high volume. In some examples, the alarm can include a mild shock to the patient via electrical pacing or transcutaneous electrical nerve stimulation (TENS) that has no effect on the patient's cardiac function but is uncomfortable enough to rouse the patient to an awakened state, when the patient is in an immobilized sleep stage. Depending upon the type of arrhythmia detected and the patient sleep stage, the patient response time can be adjusted as well. For example, if the patient is experiencing ventricular tachycardia (VT), the patient may typically have 60 seconds to respond (programmable, for example, up to 180 seconds). However, if the patient is in an immobilized sleep stage, the time to respond can be automatically increased to 90 seconds. Similarly, if the patient is experiencing ventricular fibrillation (VF), the patient may typically have 20 seconds to respond (programmable, for example, up to 55 seconds). If the patient is in an immobilized sleep stage, the time to respond can be automatically increased to 30 seconds.

In certain implementations, adjusting the cardiac arrhythmia detection parameters includes changing the thresholds at which the device provides treatment to a patient. For example, adjusting the cardiac arrhythmia detection parameters can include changing one or more of a VT onset heart rate, a VF onset heart rate, a bradycardia onset heart rate, a tachycardia onset heart rate, and an asystole onset heart rate. For example, for a particular patient, when the patient is in an immobilized sleep stage as described herein, the bradycardia onset heart rate may be adjusted from 20 bpm to 25 bpm. As the patient is less likely to awaken from the immobilized sleep stage when being treated for bradycardia, and thus less likely to shut off the treatment, the onset heart rate can be increased to initiate pacing pulses sooner when the patient is experiencing bradycardia. However, this is merely described by way of example only. In certain examples, the bradycardia onset rate can be adjusted between about 20 bpm and about 45 bpm. Similarly, a default VT onset heart rate can be about 150 bpm. When the patient is in an immobilized sleep stage, the VT onset heart rate can be lowered to about 100 bpm. In some examples, the VT onset rate can be set between a lower limit of about 100 bpm to an upper limit of the VF onset heart rate. In some examples, the default VF onset heart rate can be set to about 200 bpm. When a patient is in an immobilized sleep stage, the VF onset heart rate can be lowered to about 150 bpm. In certain examples, the adjusted VF onset heart rate can be adjusted between about 120 bpm and 200 bpm. In some examples, the asystole onset heart rate can be five average heartbeat lengths without a heartbeat (e.g., if a heartbeat is not detected for five heartbeat lengths, determine that the patient is experiencing asystole). The asystole onset heart rate can have a range of about three heartbeat lengths to about ten heartbeat lengths.

The individual cardiac arrhythmia detection parameters as described herein can be set by an authorized caregiver such as a prescriber or the patient's health care provider. In some examples, the cardiac arrhythmia detection parameters can be dynamically and automatically adjusted by the processor. For example, if there are repeated false alarms (e.g., three false alarms over a seven day period), the processor can automatically adjust one or more of the cardiac arrhythmia detection parameters. For example, if the wearable medical device is detecting that the patient is experiencing VF using a modified VF onset heart rate of 120 bpm and experiences three false alarms over a seven day period, the processor can be configured to increase the VF onset heart rate, e.g., to 135 bmp. If, using the updated VF onset heart rate, the false alarms are reduced or eliminated altogether, the processor can maintain the updated VF onset heart rate. If, however, the device continues to have false alarms, the processor can continue to update the VF onset heart rate.

In some examples, adjusting the confidence level can include adjusting a confidence level associated with identification of an arrhythmia. In certain implementations, the confidence level is used to verify treatment to be delivered to a patient prior to delivery. To calculate the confidence level, a predetermined mathematical relationship between various parameters is established and presented as a percentage. For example, the various parameters can include whether a patient response to an alarm has been received, noise values on one or more sensing electrode channels, ECG morphology match information, FFT analysis of arrhythmia, FFT analysis of heart rate, sensing electrode channel stability information, complex axis information, and other similar parameters. Each parameter can be weighted, and the confidence level can be calculated. Typically, a default confidence level should hit about 80% within a verification period (e.g., 10-30 seconds) before treatment is initiated. However, when a patient is in an immobilized sleep stage as described herein, the algorithm to calculate the confidence level can be dynamically adjusted. For example, the verification period timing can be shortened if the patient is in an immobilized sleep stage. Similarly, one or more input parameters for the confidence level algorithm can be dropped and/or one or more weights can be adjusted in the confidence level algorithm. For example, the noise values on the sensing electrode channels can be dropped from the confidence level algorithm or, conversely, the weights associated with the noise values can be lowered such that the noise values contribute less to the overall confidence level when the patient is in an immobilized sleep stage. Additionally, the confidence level threshold needed to trigger treatment can be lowered if the patient is in an immobilized sleep stage. For example, the confidence level threshold can be lowered to 75% when the patient is in an immobilized sleep stage.

Adjusting the noise threshold can include adjusting an acceptable level of noise on each of the sensing electrodes before ignoring the ECG signals being received from the sensing electrodes. For example, each sensing electrode pair channel can have an associated noise flag. When the patient is in an immobilized sleep stage, the time for noise verification on each channel can be increased. Similarly, the threshold for identifying a noisy channel can be increased when the patient is in an immobilized sleep stage. For example, the threshold for identifying a noisy channel can be increased 10%, 15%, 20%, or 25% when a patient is in an immobilized sleep stage.

Figure 5B:
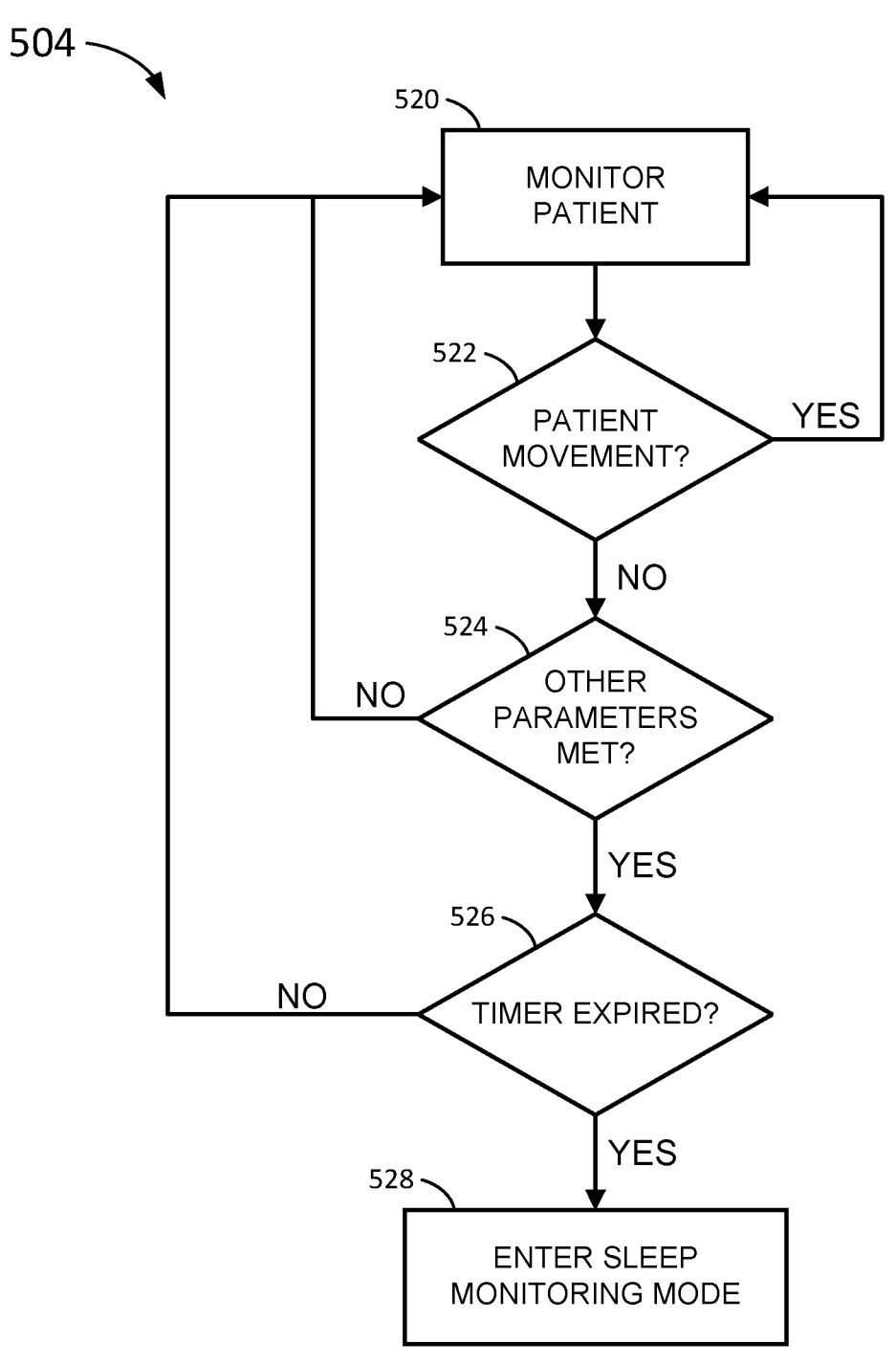
FIG. 5B illustrates additional detail of the process flow as shown in FIG. 5A, in accordance with an example of the present disclosure.

As shown in FIG. 5A and noted above, the processor can determine 504 whether a patient is asleep or is still active. Based upon this determination, the processor can switch from an active monitoring mode to a sleep monitoring mode that includes, for example, an immobilized sleep monitoring and treatment mode and a non-immobilized monitoring and treatment mode as described herein. FIG. 5B illustrates a more detailed process for determining 504 whether a patient is asleep.

As shown in FIG. 5B, the processor can monitor 520 the patient. The patient monitoring can include, for example, monitoring patient movement, patient ECG information such as heart rate, patient respiration patterns, and other similar information for the patient. Based upon the patient information, the processor can determine 522 if the patient is currently moving or performing a specific action. For example, the processor can determine 522 if the patient is walking or otherwise moving in such a manner that would indicate that the patient is not laying down or in a relaxed position to go to sleep. If the processor determines 522 that the patient is moving, the processor can continue to monitor 520 the patient. If the processor determines 522 that the patient is not moving, the processor can determine 524 whether one or more other parameters for indicating the patient is asleep are met.

For example, the processor can determine 524 whether there are any changes in the patient's heart rate and/or respiration rate. For example, a drop in a certain percentage of both heart rate and respiration rate can indicate that the patient is asleep. In certain implementations, a drop of 5% to 10% in heart rate can indicate that the patient is likely asleep. Similarly, a drop of about 10-20% in respiration rate can indicate that a patient is likely asleep. Changes in heart rate and respiration rate, in combination with limited or no motion, can provide an indication that the patient is likely asleep.

As shown in FIG. 5B, if the processor determines 524 the other parameters are not met (e.g., no change in heart rate and/or respiration rate), the processor can continue to monitor 520 the patient. If the processor determines 524 that the other parameters are met, the processor can initiate a timer. For example, the processor can initiate a 30 minute timer. In some examples, the timer can range from 15 minutes to 45 minutes. During the timer, the processor can determine 526 whether the timer has expired. If the processor determines 526 that the time has not expired, the processor can continue to monitor 520 the patient, determine 522 patient movement, and determine 524 of the other monitored parameters are met as described above. If, while determining 526 whether the timer has expired, there are any changes to the determining 522 patient movement or determining 524 whether the other parameters are met, the processor can reset or otherwise stop the timer. Otherwise, once the processor determines 526 that the timer has expired, the processor can enter 528 sleep mode and monitor the patient accordingly as described herein.

It should be noted that the processor can also monitor various other information such as time of day and patient input on, for example, a user interface associated with the wearable medical device. In certain implementations, if the patient provides an indication that they are going to sleep, the processor can alter one or more parameters associated with determining whether the patient is asleep as described above. For example, if the patient provides an indication that they are going to sleep, the processor can lower the time from a default value (e.g., 30 minutes) to a shorter value (e.g., 15 or 20 minutes). Similarly, if the processor determines that the time of day is later than a particular time (e.g., later than 10 PM), the processor can similarly alter one or more parameters associated with determining whether the patient is asleep.

Figure 5C:
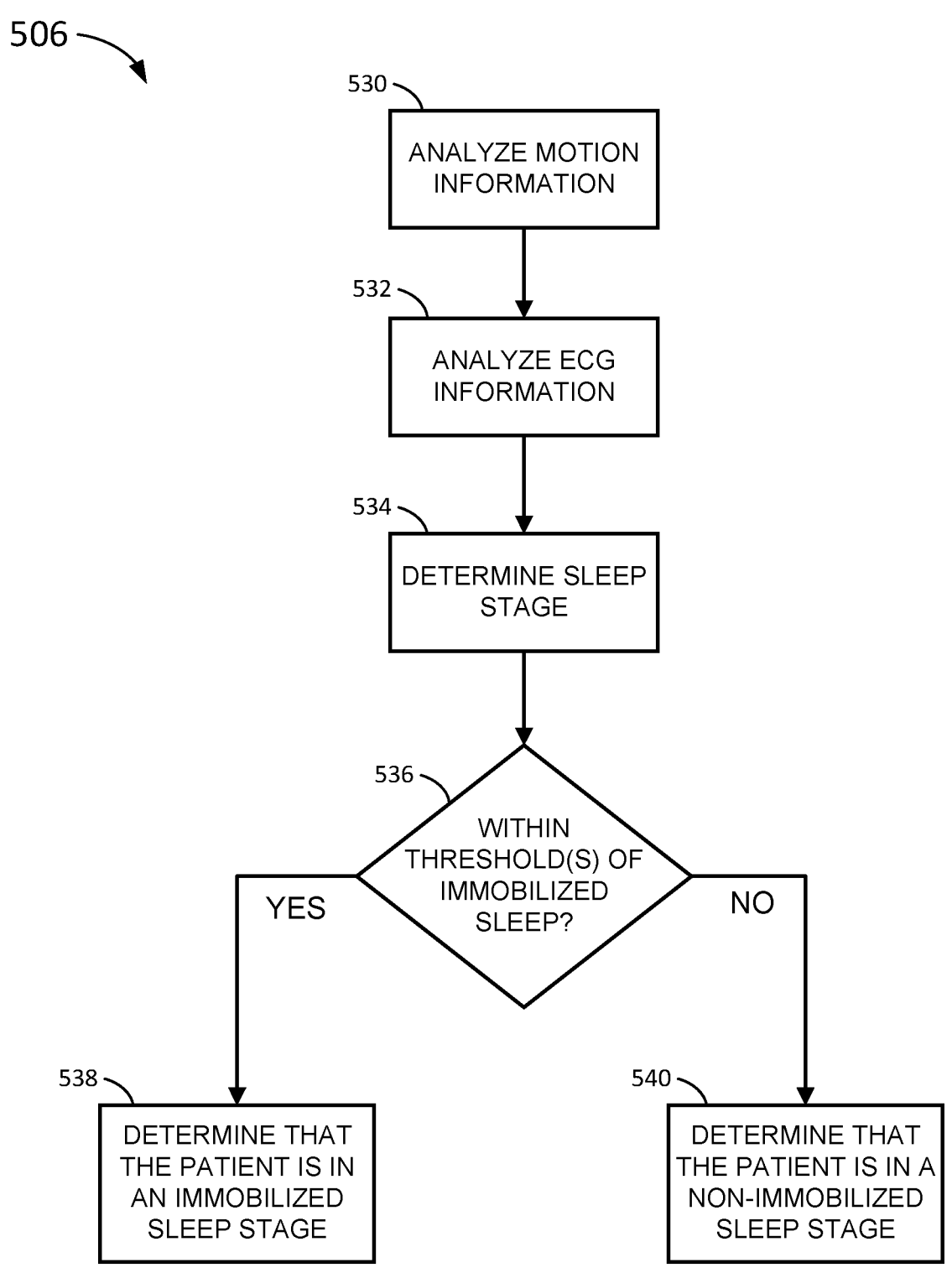
FIG. 5C illustrates additional detail of the process flow as shown in FIG. 5A, in accordance with an example of the present disclosure.

Referring back to FIG. 5A, and as noted above, once the processor determines that the patient is asleep (e.g., as shown in FIG. 5B and described above), the processor can determine 506 whether a patient is in an immobilized sleep stage. FIG. 5C illustrates a more detailed process for determining 506 whether a patient is in an immobilized sleep stage or a non-immobilized sleep stage. For example, as shown in FIG. 5C, the processor can analyze 530 the motion information and the derived motion parameters. In some examples, the motion parameters can include a rotational motion parameter that quantifies an amount of rotational motion of the patient as measured by at least one accelerometer. For example, the rotational motion of the patient can be measured and represented on a scale of zero to 360 degrees of rotation of the patient's body when sleeping. In other examples, the motion parameters can include patient respiration information, patient physical movement information, and patient body position information. However, it should be noted that determining the motion parameters solely from the motion information is provided by way of example only. In some examples, one or more motion parameters such as patient respiration information can be derived from one or more impedance-based measurements received from, for example, one or more sensing electrodes as described herein.

In one example, the motion parameter detected may be breathing-related motion using sensing based on electrical impedance tomography (EIT). EIT is a non-invasive imaging technique used for medical application as well as for non-destructive inspection of technical devices or processes. EIT was first introduced for medical imaging in the mid-1980s by Barber and Brown. For EIT imaging, electrodes are placed equidistant around a cylindrical-like object such as the human thorax. Between any two adjacent electrode pairs, a constant electric current is injected into the body under inspection while all other electrodes measure pair wise the resulting voltages at their location. By having repeated current injections and voltage measurements between all electrode pairs, a data set is established for reconstructing the body's internal structure by a mathematical operation called filtered back-projection. By reconstructing over a period of time, the patient's breathing rate can be determined and used to estimate their sleep stage. For example, the initial breathing rate at the time a person goes to sleep can be used as a baseline. If the breathing rate decreases by more than a predetermined threshold, e.g. 80% of baseline, the patient's sleep stage can be considered to be immobilized. For example, when the patient falls asleep, their breathing can be measured as 20 breathes per minute. Once the measured breathing rate for the patient reaches 16 breathes per minute (i.e., 80% of the baseline 20 breathes per minute), the patient can be considered to be in an immobilized sleep stage.

In some examples, sensors may be configured to detect the motion parameter of when a patient rolls over and "changes sides" during sleep. Changing sides while sleeping is often a very intermittent motion with longer periods of no motion but is highly indicative of a non-immobilized sleep stage. In some examples, detecting motion characterized as changing sides can be accomplished by force sensors mounted circumferentially around the patient's thorax. The force sensor can include a load cell that is coupled to signal processing and filtering circuitry and an Analog-to-Digital Converter device. In some examples, two force sensors can be mounted onto the garment of the wearable medical device as described herein, one near the sternum and the other near the spine. The force sensors can be configured to detect when the patient is lying on their front and back by which sensor has a positive force output. A patient lying on their side can be detected when neither force sensor has any weight on it and is subsequently not outputting a force output. In some implementations, four sensors may be employed with two sensors placed on the two sides of the patient in addition to the front and back. In some examples, when the force measured by the force sensor exceeds a threshold, e.g. 10% of patient body weight, then the patient is determined to be lying on that side. In some versions, in order to account for the fact that a patient's arm may be lying across the upwards-facing force sensor when the patient is lying on their side, if more than one force sensor is measuring a non-zero force then the sensor with the largest force measurement is determined to be facing downwards to the mattress surface. When the determination of the force sensor that is facing downwards changes, the patient is determined to have changed sides. In one example, when a change of sides has been detected, the patient will be considered to be in a non-immobilized state for a predetermined amount of time, e.g. 10 minutes, following the detection, even though no other motion is detected during that time period. If after the predetermined period of time, the patient has not made any additional movement (e.g., another change of sides), the patient can be considered to be in an immobilized state.

It should be noted that a predetermined time period of 10 minutes as described above in regard to measuring patient motion is provided by way of example only. In some examples, the predetermined time can include five minutes, 15 minutes, 20 minutes, 25 minutes, and 30 minutes.

In certain implementations, the motion information can include output information from one or more motion sensors such as the accelerometers (e.g., accelerometers 200 and 322 as described above). The output information can indicate movement information in each of three axes (i.e., the x-axis, the y-axis, and the z-axis) for a patient. Based upon this output information, the processor can determine whether a patient is moving as well as the distance and direction of any movement. The processor can monitor this information over a period of time to determine if the patient is motionless. For example, the processor can monitor the motion information and derived motion parameters over a period of two minutes, five minutes, seven minutes, ten minutes, thirty minutes, forty-five minutes, one hour, and other similar time periods. Based upon the analysis 530 of the motion information, the processor can determine whether the patient is motionless or, if not, how much the patient is moving in their sleep.

As further shown in FIG. 5C, the processor can be configured to analyze 532 the patient's ECG information and any derived ECG parameters as described herein. In certain implementations, the ECG parameters can include one or more of heart rate, heart rate variability, premature ventricular contraction (PVC) burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T wave variability, and ST segment changes.

For example, the processor can monitor the patient's heart rate as compared to a baseline resting heart rate threshold. Based upon the deviation of the monitored heart rate as compared to the baseline resting heart rate over a period of time, the processor can determine a percentage deviation over the period of time. For example, the processor can compare the monitored heart rate against the baseline resting heart rate threshold to determine a deviation threshold of less than 1% deviation from baseline resting heart rate, less than 2% deviation from the resting heart rate, less than 5% from the baseline resting heart rate, and other similar percentage deviations over a period of time. In some examples, the period of time can include two minutes, five minutes, seven minutes, ten minutes, thirty minutes, forty-five minutes, one hour, and other similar time periods.

In a specific example, a patient's baseline resting heart rate when in an immobilized sleep stage can be about 55 bpm. The processor can monitor the patient's current heart rate over a period of time and compare that to the baseline resting heart rate. For example, the patient's current heart rate over the past two minutes may be 57 bpm. In such an example, when compared to the baseline resting heart rate of 55 bpm, the processor can determine that the patient currently has a less than 2% deviation from the baseline resting heart rate.

It should be noted that analysis of motion and ECG information is shown in FIG. 5C by way of example only. In certain implementations, additional information such as respiratory rate information can be used to determine whether a patient is in an immobilized or a non-immobilized sleep stage.

As further shown in FIG. 5C, based upon the results of the motion and ECG information analysis, the processor can determine 534 what particular sleep stage the patient is in. For example, the processor can determine whether the patient is in one of the American Associated for Sleep Medicine (AASM) sleep stages based upon the analyzed motion and ECG information. For example, sample sleep stage information and associated motion and ECG information is shown in Table 2 by way of example only.

TABLE 2

| Stage | Heart Rate | Motion Information | Respiration (in breaths per min) | Immobilized? |
|---|---|---|---|---|
| Baseline Awake | 85 bpm | Near Constant | 20 | No |
| Baseline Immobilized Sleep | 55 bpm | No movement for more than 5 minutes | 12 | Yes |
| N1 Sleep Stage | 70 bpm | Movement | 18 | No |
| N2 Sleep Stage | 60 bpm | No movement for 1 minute | 16 | No |
| N3 Sleep Stage | 57 bpm | No movement for 3 minutes | 14 | Yes |
| N4 Sleep Stage | 55 bpm | No movement for 5 minutes | 12 | Yes |
| REM | Varies between 55-65 bpm | No movement for 5 minutes | Varies between 12-15 | Yes |

As shown in Table 2, certain sleep stages such as N3, N4, and REM can be considered immobilized sleep stages. These stages represent a deep sleep (N3), a slow-wave sleep (N4), or a dreaming sleep (REM) stage where the body is immobilized. As also shown in Table 2, certain sleep stages such as N1 and N2, as well as consciousness or wakefulness, can be considered non-immobilized sleep stages. These stages represent a relaxed wakefulness (N1) and a light sleep (N2) stage.

Each sleep stage is linked to specific brain waves and neuronal activity. Most patients cycle through all stages of non-REM and REM sleep several times during a typical night. In examples, patients undergo increasingly longer, deeper REM periods occurring towards morning.

In one hypothetical scenario, sleep stages can occur as follows. Stage 1 non-REM sleep may be characterized as changeover from wakefulness to sleep. During this short period (e.g., lasting around 5-15 minutes) of relatively light sleep, the patient's heartbeat, breathing, and eye movements slow, and muscles relax with occasional twitches. In this period, the patient's brain waves begin to slow from daytime wakefulness patterns.

During stage 2 non-REM sleep, the patient undergoes a period of light sleep before the patient enters deeper sleep. The patient's heartbeat and breathing slow, and muscles relax even further than state 1 non-REM sleep. In stage 2 non-REM sleep, the patient's body temperature drops and eye movements stop. Brain wave activity slows but may be marked by brief bursts of electrical activity. The patient spends more of the patient's repeated sleep cycles in stage 2 sleep than in other sleep stages.

During stage 3 non-REM sleep, the patient enters a period of deep sleep needed to feel refreshed in the morning. This stage occurs in longer periods during the first half of the night. The patient's heartbeat and breathing slow to their lowest levels during this stage of sleep. In stage 3 non-REM sleep, the patient's muscles are relaxed, and it may be difficult to awaken the patient during this stage with audio or vibrational stimulation relative to the other sleep stages. Further, this stage is characterized by the brain waves become even slower relative to the other sleep stages.

Continuing the hypothetical scenario, REM sleep can typically occur about 90 minutes after falling asleep (e.g., 90 minutes after entering stage 1 non-REM sleep). The patient's eyes move rapidly from side to side behind closed eyelids. Mixed frequency brain wave activity becomes closer to that seen in wakefulness. The patient's breathing becomes faster and irregular, and the patient's heart rate and blood pressure increase to near waking levels. Most of the patient's dreaming occurs during this period of REM sleep. The patient's arms and leg muscles become temporarily immobilized, which tends to prevent the patient from acting the patient's dreams.

Two internal biological mechanisms, circadian rhythm and homeostasis, work together to regulate when a patient is awake and asleep. Circadian rhythms direct a wide variety of functions from daily fluctuations in wakefulness to body temperature, metabolism, and the release of hormones. This mechanism controls the timing of sleep and causes a patient to feel sleepy at night and tendency to awake in the morning. For implementations herein, it is assumed that patient's bodies typically follow a biological clock, based on a roughly 24-hour day, and thus control most circadian rhythms. It is understood, however, that circadian rhythms may synchronize with environmental cues (e.g., light, temperature) about the actual time of day.

Sleep-wake homeostasis keeps track of a patient's need for sleep. The homeostatic sleep drive reminds a patient's body to sleep after a certain time and regulates sleep intensity. The sleep drive gets stronger every hour a patient is awake and causes the patient to sleep longer and more deeply after a period of sleep deprivation. Factors that influence a patient's sleep-wake needs include medical conditions, medications, stress, sleep environment, and what the patient has had to eat and drink.

Referring again to FIG. 5C, as noted above, the processor can be further configured to determine 534 the current sleep stage for the patient. Based upon the current sleep stage, the processor can determine 536 whether the current sleep stage is within the threshold of being considered immobilized sleep. For example, as shown in Table 2, each of sleep stages N3, N4, and REM are considered immobilized sleep stages. As such, if the processor determines 534 that the patient is in one of sleep stage N3, N4, or REM, the processor can determine 536 that the patient is within the threshold of immobilized sleep and identify 538 the patient as being in an immobilized sleep stage. Conversely, if the processor determines 534 that the patient is in one of sleep stage N1 or N2, the processor can determine 536 that the patient is not within the threshold of immobilized sleep and identify 540 the patient as being in a non-immobilized sleep stage.

Figure 6:
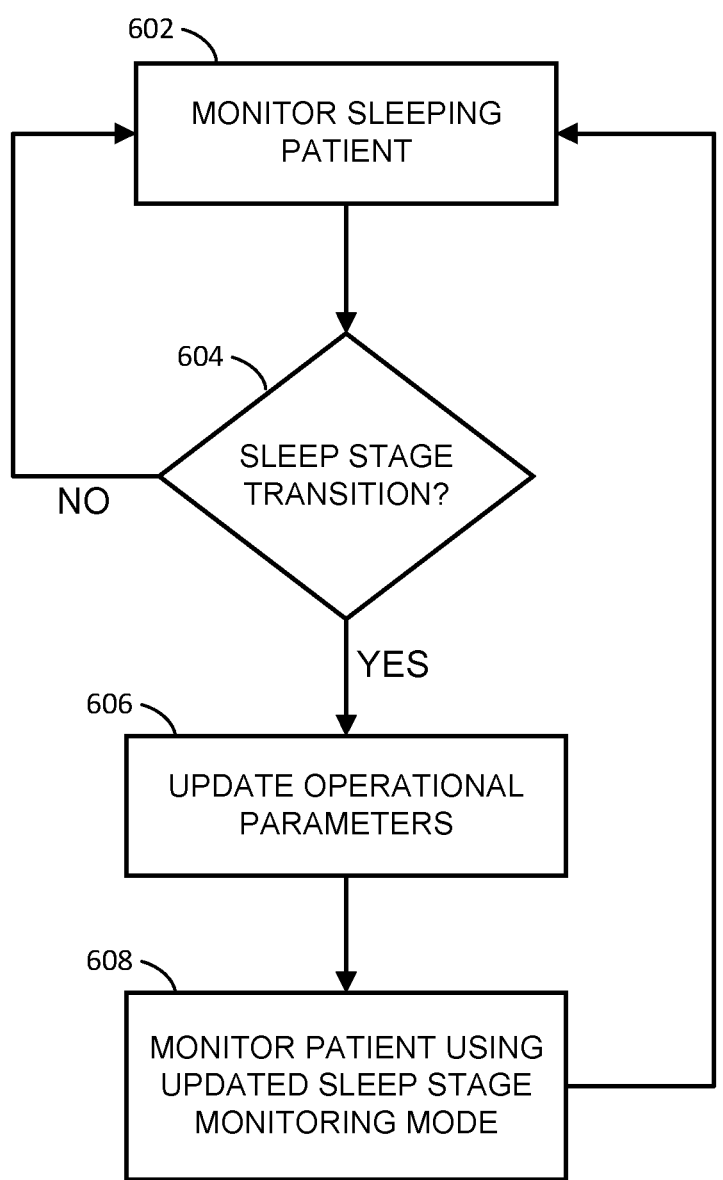
FIG. 6 illustrates a process flow for determining whether a patient has transitioned between sleep stages, in accordance with an example of the present disclosure.

During sleep, the patient can transition between immobilized sleep stages and non-immobilized sleep stages. During such transitions, the processor of the medical device controller can be configured to determine that the patient has transitioned between stages and, if necessary, adjust the monitoring and treatment mode as described herein accordingly. For example, FIG. 6 illustrates a sample process 600 for determining whether a patient has transitioned between sleep stages. As shown in FIG. 6, the processor can monitor 602 the sleeping patient. For example, the processor can monitor 602 the patient's motion information, the patient's ECG information, and information for the patient such as respiratory information. Based upon analysis of the patient's information, the processor can determine 604 whether the patient has transitioned from one sleep stage to another. For example, the processor can determine 604 whether the patient has transitioned from an N2 sleep stage to an N3 sleep stage. In such an example, the processor can update 606 the operational parameters for the medical device and monitor 608 the patient using the updated sleep stage mode. In this example, the processor can monitor 608 the patient using the immobilized sleep monitoring and treatment mode as described herein. However, transitioning from a non-immobilized sleep stage (e.g., N2) to an immobilized sleep stage (e.g., N3) as described above is by way of example only. In certain examples, the patient can transition from an immobilized sleep stage (e.g., N4) to a non-immobilized sleep stage (e.g., N1). In such an example, the processor can update 606 the operational parameters such that the processor can monitor 608 the patient using the non-immobilized monitoring and treatment mode as described herein.

As further shown in FIG. 6, in some examples, the processor can determine 604 that the patient has not transitioned between sleep stages. In such an example, the processor can continue to monitor 602 the sleeping patient for changes in the patient's monitor information.

In certain implementations, when a patient is in an immobilized sleep stage, it may be advantageous to perform additional monitoring. For examples, when using RF-based monitoring, the quality of any measured information can be improved if the patient remains stationary when the information is being collected. As such, it can be advantageous to perform RF-based monitoring when a patient is in an immobilized sleep stage.

Figure 7:
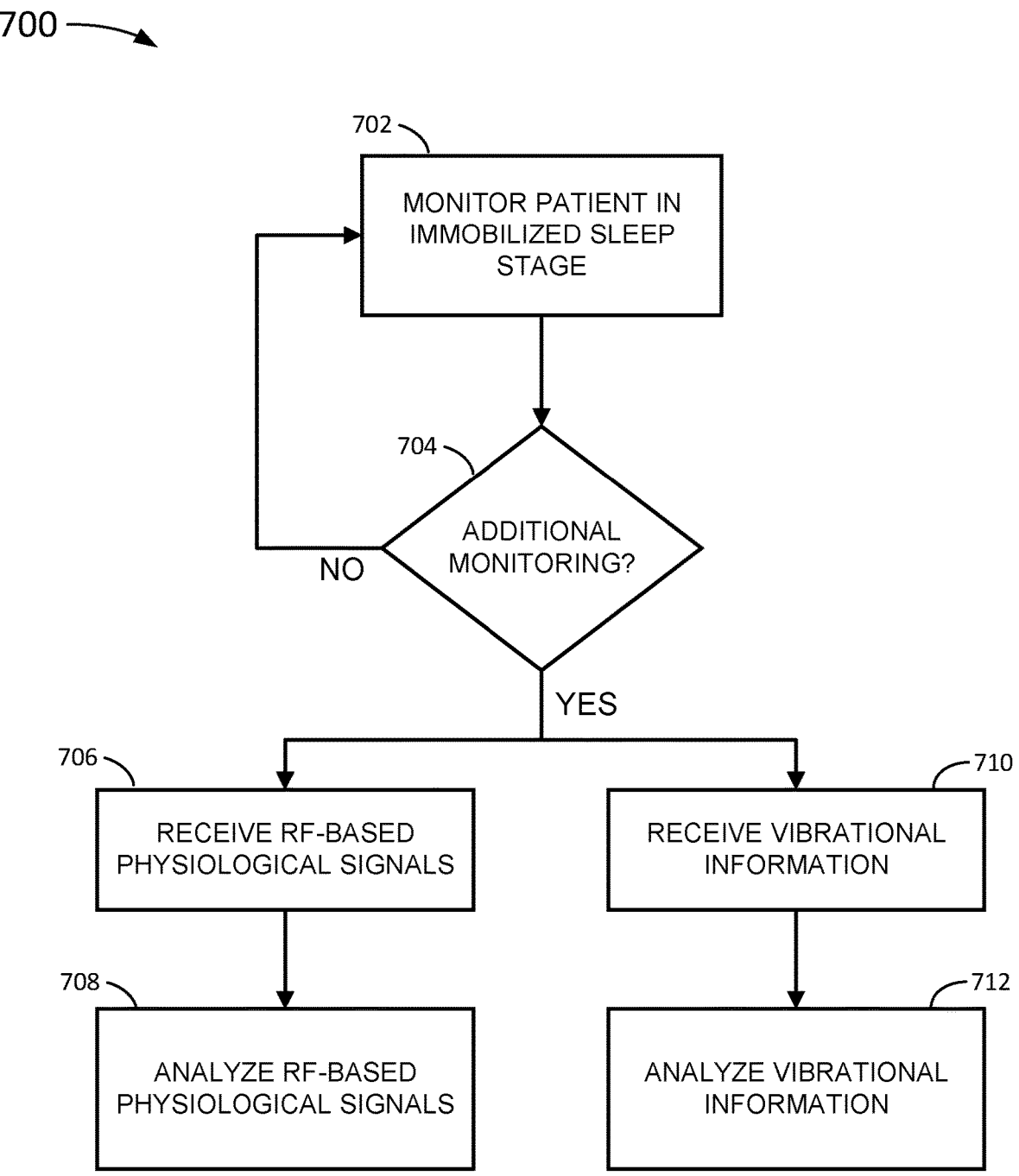
FIG. 7 illustrates a process flow for performing additional monitoring when a patient is in an immobilized sleep stage, in accordance with an example of the present disclosure.

FIG. 7 illustrates a sample process 700 for performing additional monitoring when a patient is in an immobilized sleep stage. As shown in FIG. 7, the processor can monitor 702 the patient and confirm that the patient is in an immobilized sleep stage. Additionally, the processor can determine 704 that the patient is to have additional monitoring performed. For example, the medical device can be configured to perform additional testing once a week. If the processor determines 704 that the patient does not require any additional testing, the processor can continue to monitor 702 the patient as described herein. However, if the processor does determine 704 that the patient is to have additional monitoring, the processor can monitor one or more additional non-ECG signals as described herein.

For example, as shown in FIG. 7, the processor can receive 706 RF-based physiological signals from an RF sensor as described above. The processor can analyze the RF-based physiological signals to determine additional patient information such as heart wall movement information and thoracic fluid level information. Additionally or alternatively, the processor can be further configured to receive 710 vibrational information from a vibrational sensor as described above. The processor can analyze 712 the vibrational information to determine various information such as cardiovibrational information for the patient. Based upon the cardiovibrational information, the processor can determine one or more electromechanical parameters of the patient's heart.

Figure 8:
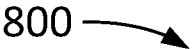
FIG. 8 illustrates a process flow for establishing baseline sleep stage information for a patient, in accordance with an example of the present disclosure.
Figure 8:
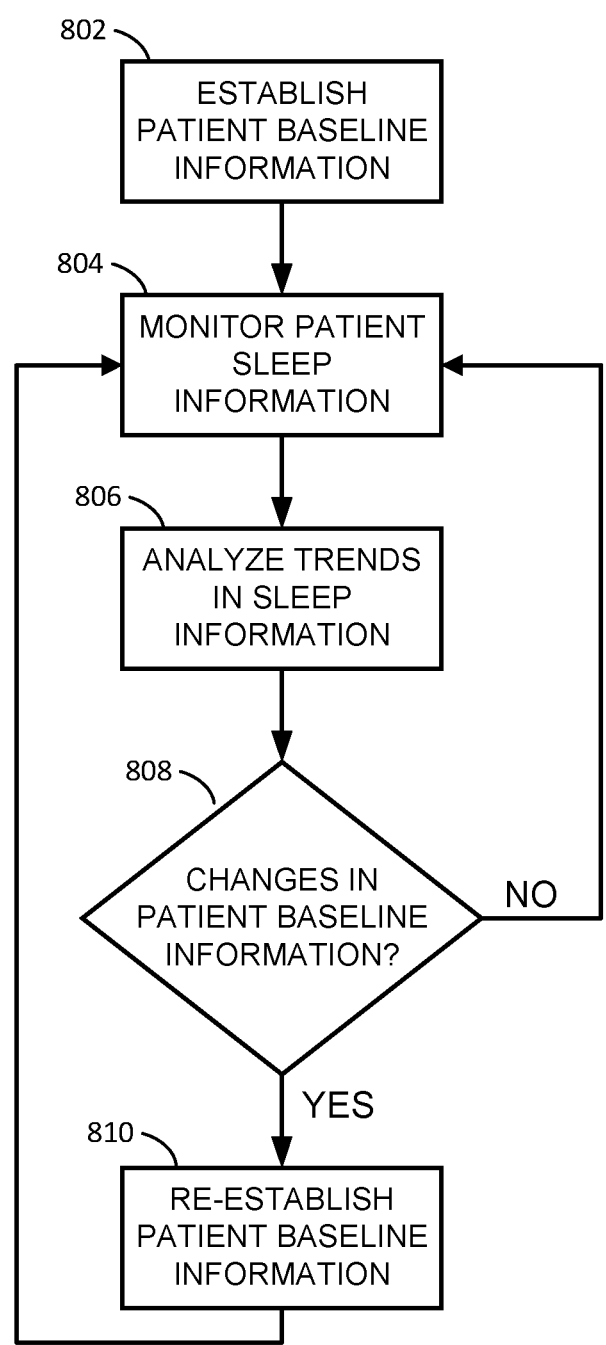

As noted above, to determine whether a patient is in an immobilized sleep stage or a non-immobilized sleep stage, the processor can compare current patient information against baseline information. FIG. 8 illustrates a sample process 800 for collecting the patient baseline information and re-establishing the patient's baseline information at regular intervals. For example, the patient baseline information can be re-established every week, every two weeks, every three weeks, every month, and at other similar intervals.

As shown in FIG. 8, the processor can establish 802 initial patient baseline information. For example, the processor can collect and analyze patient information over a period of two to three days following the initial prescription and wearing of the wearable medical device as described herein. Based upon the collected information, the processor can determine various information such as active heart rate and motion information, sleeping heart rate and motion information, respiratory information, and other similar patient information. Based upon the determined information, the processor can establish 802 the initial patient baseline information for the patient. Based upon the initial patient baseline information, the processor can determine one or more sleep stage thresholds such as those shown in Table 2 above to be used for determining and identifying the current sleep stage of a sleeping patient.

Once the baseline information has been established, the processor can monitor 804 the patient sleep information such as heart rate information, motion information, and respiratory information collected while the patient is asleep. The processor can analyze 806 the monitored information to determining any trends in the sleep information. For example, as a patient's cardiac health increases, the patient's baseline resting heart rate can decrease. As such, over time, the processor can continue to analyze 806 the trends in the sleep information. After a period of time (e.g., 1 week) or if the changes in the sleep information exceed a particular threshold (e.g., a piece of information deviates from the baseline by more than 10% a certain number of times over the period of monitoring), the processor can determine 808 whether to make changes to the patient baseline information. If the processor does not determine 808 to make any changes to the baseline information, the processor can continue to monitor 804 the patient using the existing baseline information. However, if the processor does determine 808 to make changes to the patient baseline information, the processor can re-establish 810 one or more pieces of the baseline information based upon the updated monitored patient information. As further shown in FIG. 8, the processor can continue to monitor 804 the patient sleep information using the updated baseline information.

Figure 9A:
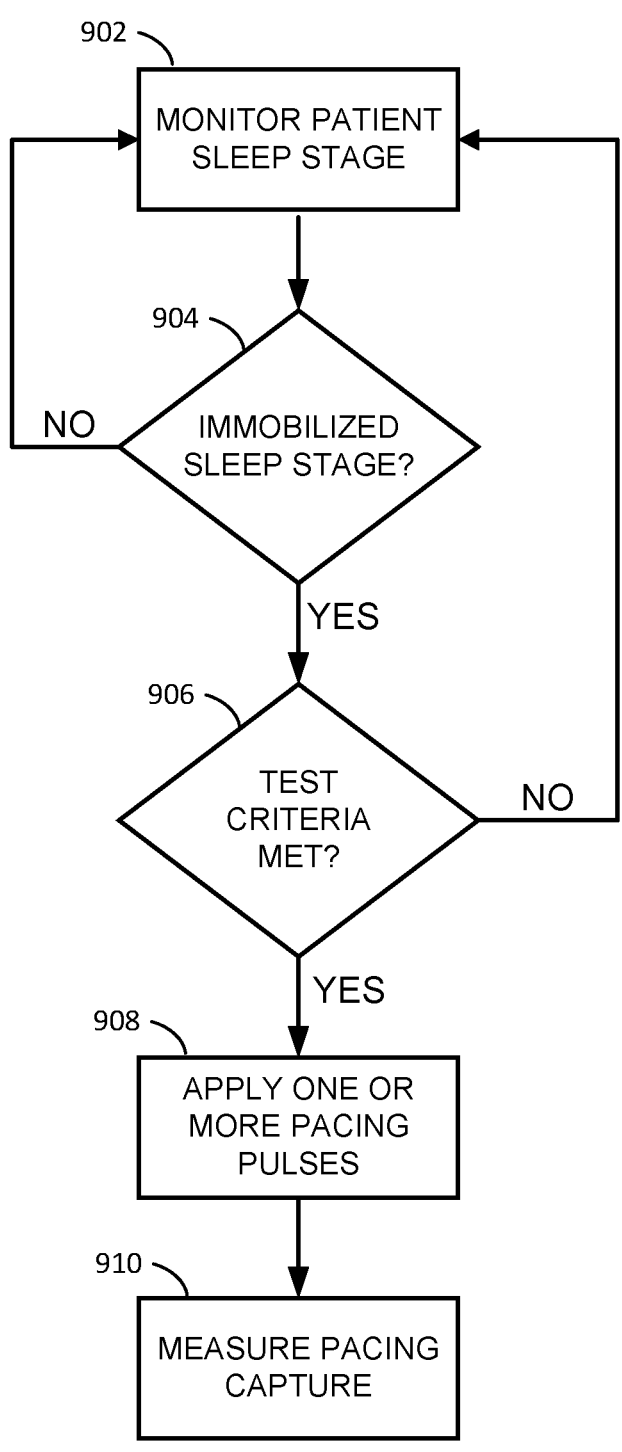
FIG. 9A illustrates a process flow for measuring pacing capture when a patient is in an immobilized sleep stage, in accordance with an example of the present disclosure.
Figure 9B:
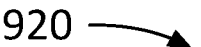
FIG. 9B illustrates a process flow for measuring heart rate turbulence when a patient is in a particular sleep stage, in accordance with an example of the present disclosure.
Figure 9B:
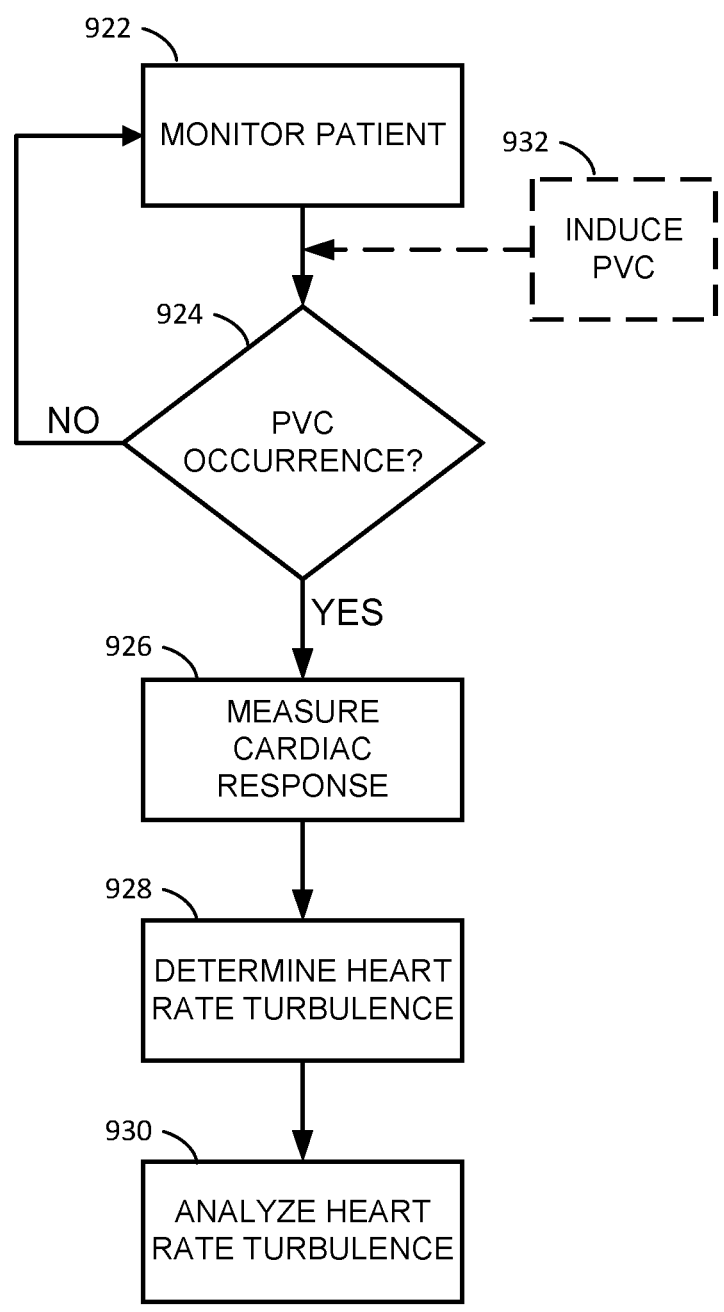

As noted above, additional monitoring of a patient can be performed when the patient is in an immobilized sleep stage. As shown in FIGS. 9A and 9B, when a patient is in a certain sleep stage, additional testing and monitoring of the patient can be performed. For example, as shown in FIG. 9A, patient capture of an applied pacing pulse can be measured when a patient is in an immobilized sleep stage. In such a situation, the likelihood of the patient reacting poorly to the test or shutting the device off mid-test is reduced as a result of the patient being in the immobilized sleep stage.

As shown in FIG. 9A, process 900 includes the processor monitoring 902 the patient sleep stage information. Based upon the monitored sleep stage information, the processor can determine 904 whether the patient is in an immobilized sleep stage. If the processor determines 904 that the patient is not in an immobilized sleep stage, the processor can continue to monitor 902 the patient sleep stage information. However, if the processor does determine 904 that the patient is in an immobilized sleep stage, the processor can determine 906 whether any additional testing criteria are met for the pacing capture test. For example, if the patient's heart rate is below a certain threshold (e.g., more than 10% below the patient's baseline resting heart rate), the processor may determine 906 that the test should not be performed and continue to monitor 902 the patient's sleep stage information. Conversely, if the processor does determine 906 that any additional criteria are met, the processor can initiate the testing procedure and apply 908 one or more pacing pulses to the patient via one or more therapy electrodes as described herein. After application of the one or more pacing pulses, the processor can monitor the patient's ECG or information from another sensor such as a pulse oximeter information to measure 910 pacing capture information for the patient's heart in response to the applied one or more pacing pulses. In one example, the protocol for the pacing capture test is as follows: 1) set pace amplitude to 50 mA; 2) deliver two pace pulses; 3) check via ECG or pulse oximeter information for pace capture of one or both pace pulses; 4) if capture, then set pacing capture level to pace amplitude plus 10 mA; 5) if no capture, increase pace amplitude by 10 mA and repeat 1-4.

In addition to measuring pacing capture, a patient's response to a premature ventricular contraction (PVC) can be measured when the patient is in a particular sleep stage. A PVC is an extra heartbeat originating in one of the ventricles and disrupts the heart's regular rhythm. By measuring the time required by the heart to return to the normal rhythm, a heart rate turbulence value for the heart can be determine and later analyzed to determine additional information related to cardiac health for a patient.

As shown in FIG. 9B, process 920 can include collecting information related to and analyzing heart rate turbulence. The processor 920 includes the processor monitoring 922 the patient information. During monitoring, the processor can determine 924 if the patient has experienced a PVC. If the processor does not determine that the patient has experienced a PVC, the processor can continue to monitor the patient. However, if the processor does determine 924 that a patient has experienced a PVC, the processor can measure 926 the patient's cardiac response to the PVC by monitoring changes in the ECG signals of the patient. Based upon the cardiac response, the processor can determine 928 a heart rate turbulence value for the patient based upon the changes in the ECG signal and store the heart rate turbulence value. The processor, or another similar processing device, can then analyze the heart rate turbulence value to determine any changes in the patient's cardiac health. In certain implementations, if the patient is in an immobilized sleep stage, the processor can induce 932 a PVC in the patient via application of a pacing pulse as described above to determine the heart rate turbulence value.

Additionally, in certain implementations, information about the patient's sleep stage and position can be used to determine optimized sensing electrode pairings. For example, if the patient is laying in a position where one particular sensing electrode is likely to be pressed firmly against the patient's body, that particular sensing electrode may be providing a clear and highly reliable signal. For example, if the patient is lying on their right side, a sensing electrode positioned near the patient's right hip may be pressed against the patient's body and likely providing a clear signal. Conversely, a sensing electrode positioned near the patient's left hip may be held in place only by the elasticity of the garment and not contacting the patient's skin as tightly as the right hip electrode and, as such, not providing as clear or reliable a signal.

In certain implementations, one or more force sensors adjacent to, or integral to the ECG sensing electrodes, can be configured to sense when a sufficient amount of force is applied to the ECG sensing electrode for adequate ECG monitoring. In some examples, that minimum applied force threshold is 0.2 lbs/in². In other examples, the minimum applied force threshold can be set to 0.5 lbs/in², 1.0 lbs/in², 2.0 lbs/in², 2.5 lbs/in², and 5.0 lbs/in². This is particularly important with sensing electrodes that are considered capacitive, high-impedance electrodes. High impedance sensing electrodes can be are susceptible to noise caused by rubbing against the patient's skin since they are dry electrodes, as well as rubbing of the back surface of the sensing electrodes against the patient's clothing or bedding material while sleeping. One of the main causes of this type of noise is due to the triboelectric effect. The triboelectric effect (also known as triboelectric charging) is a type of contact electrification on which certain materials become electrically charged after they are separated from a different material with which they were in contact. Due to the high impedance of the ECG sensing electrode, the charge transfer due to the triboelectric effect can result in noise voltage. In some examples the motion sensor capable of measuring a motion parameter is a rubbing motion sensor that detects lateral motion along a surface. Similar to the force sensors described above, the rubbing motion sensor can be adjacent to or integral to the ECG sensing electrodes to most closely approximate the rubbing conditions on the ECG electrodes. In some implementations, there can be two rubbing sensors such that one sensor faces the patient and the other sensor faces away from the patient toward the bedding materials. The rubbing motion sensor may be implemented as a micro-electromechanical system (MEMS) microphone, for instance a voice pickup bone sensor (VPU) such as those manufactured by Sonion (Denmark). Alternatively, the rubbing motion sensor can be implemented as a standard electret microphone, for instance the 50GC31 as manufactured by Sonion, or a MEMS microphone such as the P11AC03 as manufactured by Sonion. With the rubbing motion sensor, triboelectric-induced noise can be estimated via measurement of acoustic or vibrational energy induced by the rubbing. In one example, the processor measures the RMS output of the rubbing motion sensor and determines the sleep stage to be non-immobilized if that RMS energy exceeds a predetermined threshold that indicates potential movement of the patient during sleep. For example, when the RMS energy is a non-zero value, the output of the rubbing motion sensor can indicate that the patient is in a non-immobilized sleep stage. Conversely, if the RMS energy is zero (or within a certain range of zero such as plus or minus 0.05 J of energy) the patient can be determined to be in an immobilized sleep stage.

Figure 10:
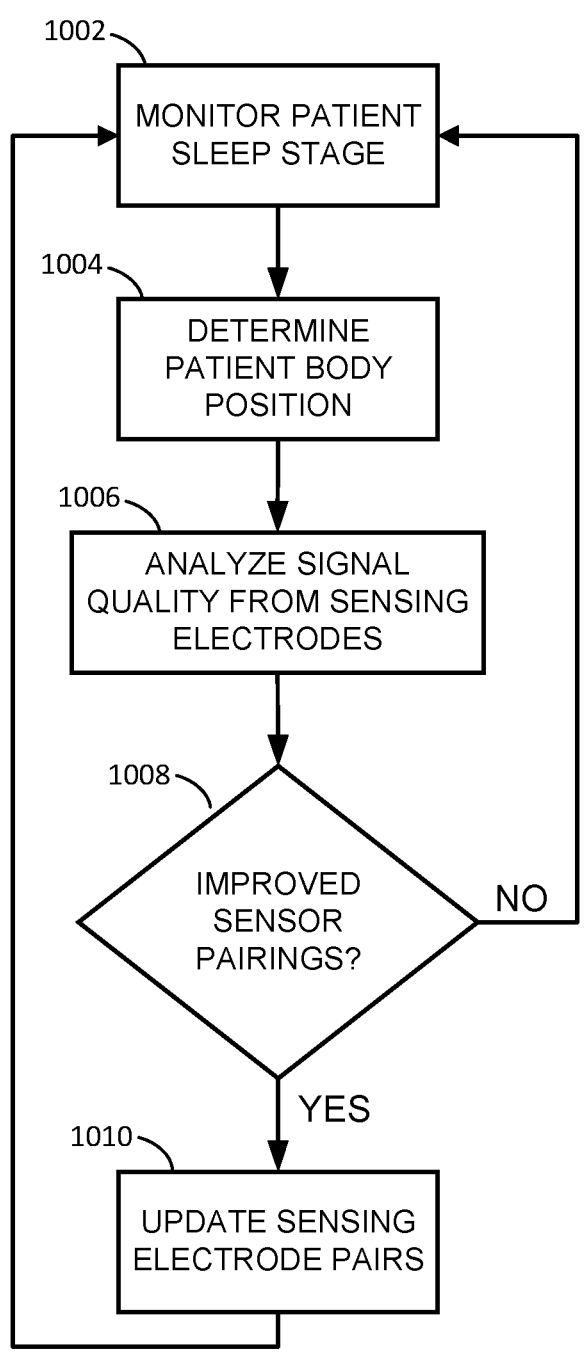
FIG. 10 illustrates a process flow for optimizing sensing electrode pairs when a patient is in a particular sleep stage, in accordance with an example of the present disclosure.

As shown in FIG. 10, process 1000 can include updating sensing electrode pairs for a sleeping patient. As shown, process 1000 can include the processor monitoring 1002 the patient's sleep stage. During the monitoring, the processor can also determine 1004 the patient's body position based upon accelerometer data received in the motion signals as described hereinabove. Additionally, the processor can further analyze 1006 the signal quality from each of the sensing electrodes. Based upon the position information and the signal quality analysis, the processor can determine 1008 whether there are any improved sensing electrode pairings possible. If the processor determines 1008 that there are no improved sensing electrode pairs (e.g., sensing electrode pairs that will result in lower overall noise and higher overall signal quality), the processor can continue to monitor 1002 the patient using the existing sensing electrode pairs. Conversely, if the processor determines 1008 that there are improved sensing electrode pairings available, the processor can update 1010 the sensing electrode pairs and monitor 1002 the patient using the updated sensing electrode pairs.

The teachings of the present disclosure can be generally applied to external medical monitoring and/or treatment devices that include one or more sensors as described herein. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other HCP provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other non-ECG physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T wave variability, and ST segment changes.

As noted above, FIG. 3 illustrates an example component-level view of a medical device controller 300 included in, for example, a wearable medical device. As further shown in FIG. 3, the therapy delivery circuitry 302 can be coupled to one or more electrodes 320 configured to provide therapy to the patient. For example, the therapy delivery circuitry 302 can include, or be operably connected to, circuitry components that are configured to generate and provide an electrical therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 318) to provide, for example, at least one therapeutic shock to the patient including one or more pacing, cardioversion, or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 302 can be configured to perform the switching and pulse delivery operations, e.g., under control of the processor 318. As the energy is delivered to the patient, the amount of energy being delivered can be tracked. For example, the amount of energy can be kept to a predetermined constant value even as the pulse waveform is dynamically controlled based on factors such as the patient's body impedance when the pulse is being delivered.

In certain examples, the therapy delivery circuitry 302 can be configured to deliver a set of cardioversion pulses to correct, for example, an improperly beating heart. When compared to defibrillation as described above, cardioversion typically includes a less powerful shock that is delivered at a certain frequency to mimic a heart's normal rhythm.

The data storage 304 can include one or more of non-transitory computer-readable media, such as flash memory, solid state memory, magnetic memory, optical memory, cache memory, combinations thereof, and others. The data storage 304 can be configured to store executable instructions and data used for operation of the medical device controller 300. In certain examples, the data storage can include executable instructions that, when executed, are configured to cause the processor 318 to perform one or more operations. In some examples, the data storage 304 can be configured to store information such as ECG data as received from, for example, the sensing electrode interface.

In some examples, the network interface 306 can facilitate the communication of information between the medical device controller 300 and one or more other devices or entities over a communications network. For example, where the medical device controller 300 is included in an ambulatory medical device, the network interface 306 can be configured to communicate with a remote computing device such as a remote server or other similar computing device. The network interface 306 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 300. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 308 can include one or more physical interface devices such as input devices, output devices, and combination input/output devices and a software stack configured to drive operation of the devices. These user interface elements can render visual, audio, and/or tactile content. Thus, the user interface 308 can receive input or provide output, thereby enabling a user to interact with the medical device controller 300.

The medical device controller 300 can also include at least one rechargeable battery 310 configured to provide power to one or more components integrated in the medical device controller 300. The rechargeable battery 310 can include a rechargeable multi-cell battery pack. In one example implementation, the rechargeable battery 310 can include three or more 2200 mAh lithium ion cells that provide electrical power to the other device components within the medical device controller 100. For example, the rechargeable battery 310 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 300.

The sensor interface 312 can include physiological signal circuitry that is coupled to one or more sensors configured to monitor one or more physiological parameters of the patient. As shown, the sensors can be coupled to the medical device controller 300 via a wired or wireless connection. The sensors can include one or more ECG sensing electrodes 322, and non-ECG physiological sensors 323 such as vibration sensor 324, tissue fluid monitors 326 (e.g., based on ultra-wide band RF devices), and motion sensors (e.g., accelerometers, gyroscopes, and/or magnetometers). In some implementations, the sensors can include a plurality of conventional ECG sensing electrodes in addition to digital sensing electrodes.

The sensing electrodes 322 can be configured to monitor a patient's ECG information. For example, by design, the digital sensing electrodes 322 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 322 can be used with an electrolytic gel dispersed between the electrode surface and the patient's skin. In certain implementations, the electrodes 322 can be dry electrodes that do not need an electrolytic material. As an example, such a dry electrode can be based on tantalum metal and having a tantalum pentoxide coating as is described above. Such dry electrodes can be more comfortable for long term monitoring applications.

Referring back to FIG. 3, the vibration sensors 324 can be configured to detect cardiac or pulmonary vibration information. For example, the vibration sensors 324 can detect a patient's heart valve vibration information. For example, the vibration sensors 324 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensors 324 can also be configured to detect heart wall motion, for instance, by placement of the sensor in the region of the apical beat. The vibration sensors 324 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 324 can also include a multi-channel accelerometer, for example, a three-channel accelerometer configured to sense movement in each of three orthogonal axes such that patient movement/body position can be detected and correlated to detected cardio-vibration information. The vibration sensors 324 can transmit information descriptive of the cardio-vibration information to the sensor interface 312 for subsequent analysis.

The tissue fluid monitors 326 can use radio frequency (RF) based techniques to assess fluid levels and accumulation in a patient's body tissue. For example, the tissue fluid monitors 326 can be configured to measure fluid content in the lungs, typically for diagnosis and follow-up of pulmonary edema or lung congestion in heart failure patients. The tissue fluid monitors 326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 326 can transmit information descriptive of the tissue fluid levels to the sensor interface 312 for subsequent analysis.

In certain implementations, the cardiac event detector 316 can be configured to monitor a patient's ECG signal for an occurrence of a cardiac event such as an arrhythmia or other similar cardiac event. The cardiac event detector can be configured to operate in concert with the processor 318 to execute one or more methods that process received ECG signals from, for example, the sensing electrodes 322 and determine the likelihood that a patient is experiencing a cardiac event. The cardiac event detector 316 can be implemented using hardware or a combination of hardware and software. For instance, in some examples, cardiac event detector 316 can be implemented as a software component that is stored within the data storage 304 and executed by the processor 318. In this example, the instructions included in the cardiac event detector 316 can cause the processor 318 to perform one or more methods for analyzing a received ECG signal to determine whether an adverse cardiac event is occurring. In other examples, the cardiac event detector 316 can be an application-specific integrated circuit (ASIC) that is coupled to the processor 318 and configured to monitor ECG signals for adverse cardiac event occurrences. Thus, examples of the cardiac event detector 316 are not limited to a particular hardware or software implementation.

In some implementations, the processor 318 includes one or more processors (or one or more processor cores) that each are configured to perform a series of instructions that result in manipulated data and/or control the operation of the other components of the medical device controller 300. In some implementations, when executing a specific process (e.g., cardiac monitoring), the processor 318 can be configured to make specific logic-based determinations based on input data received and be further configured to provide one or more outputs that can be used to control or otherwise inform subsequent processing to be carried out by the processor 318 and/or other processors or circuitry with which processor 318 is communicatively coupled. Thus, the processor 318 reacts to specific input stimulus in a specific way and generates a corresponding output based on that input stimulus. In some example cases, the processor 318 can proceed through a sequence of logical transitions in which various internal register states and/or other bit cell states internal or external to the processor 318 can be set to logic high or logic low. As referred to herein, the processor 318 can be configured to execute a function where software is stored in a data store coupled to the processor 318, the software being configured to cause the processor 118 to proceed through a sequence of various logic decisions that result in the function being executed. The various components that are described herein as being executable by the processor 318 can be implemented in various forms of specialized hardware, software, or a combination thereof. For example, the processor 318 can be a digital signal processor (DSP) such as a 24-bit DSP. The processor 318 can be a multi-core processor, e.g., having two or more processing cores. The processor 318 can be an Advanced RISC Machine (ARM) processor such as a 32-bit ARM processor or a 64-bit ARM processor. The processor 318 can execute an embedded operating system, and include services provided by the operating system that can be used for file system manipulation, display & audio generation, basic networking, firewalling, data encryption, and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 318 of the controller 300 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 11A:
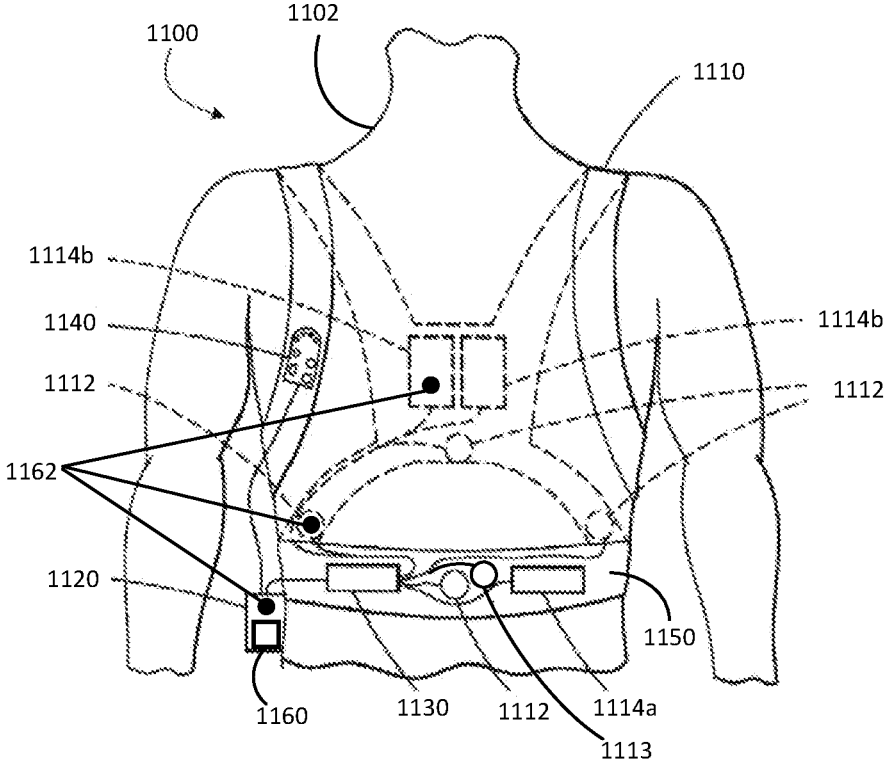
FIGS. 11A-11D illustrate sample ambulatory medical devices that may be prescribed to a heart failure patient, in accordance with an example of the present disclosure.

FIG. 11A illustrates an example medical device 1100 that is external, ambulatory, and wearable by a patient 1102, and configured to implement one or more configurations described herein. For example, the medical device 1100 can be a non-invasive medical device configured to be located substantially external to the patient. Such a medical device 1100 can be, for example, an ambulatory medical device that is capable of and designed for moving with the patient as the patient goes about his or her daily routine. For example, the medical device 1100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1100 can include one or more of the following: a garment 1110, one or more ECG sensing electrodes 1112, one or more non-ECG physiological sensors 1113, one or more therapy electrodes 1114a and 1114b (collectively referred to herein as therapy electrodes 1114), a medical device controller 1120 (e.g., controller 300 as described above in the discussion of FIG. 3), a connection pod 1130, a patient interface pod 1140, a belt 1150, or any combination of these. In some examples, at least some of the components of the medical device 1100 can be configured to be affixed to the garment 1110 (or in some examples, permanently integrated into the garment 1110), which can be worn about the patient's torso.

The medical device controller 1120 can be operatively coupled to the sensing electrodes 1112, which can be affixed to the garment 1110, e.g., assembled into the garment 1110 or removably attached to the garment, e.g., using hook and loop fasteners. In some implementations, the sensing electrodes 1112 can be permanently integrated into the garment 1110. The medical device controller 1120 can be operatively coupled to the therapy electrodes 1114. For example, the therapy electrodes 1114 can also be assembled into the garment 1110, or, in some implementations, the therapy electrodes 1114 can be permanently integrated into the garment 1110. In an example, the medical device controller 1120 includes a patient user interface 1160 to allow a patient interface with the externally-worn device. For example, the patient can use the patient user interface 1160 to respond to activity related questions, prompts, and surveys as described herein.

Component configurations other than those shown in FIG. 11A are possible. For example, the sensing electrodes 1112 can be configured to be attached at various positions about the body of the patient 1102. The sensing electrodes 1112 can be operatively coupled to the medical device controller 1120 through the connection pod 1130. In some implementations, the sensing electrodes 1112 can be adhesively attached to the patient 1102. In some implementations, the sensing electrodes 1112 and at least one of the therapy electrodes 1114 can be included on a single integrated patch and adhesively applied to the patient's body.

The sensing electrodes 1112 can be configured to detect one or more cardiac signals. Examples of such signals include ECG signals and/or other sensed cardiac physiological signals from the patient. In certain examples, as described herein, the non-ECG physiological sensors 1113, such as accelerometers, vibrational sensors, RF-based sensors, and other measuring devices, are for recording additional non-ECG physiological parameters. For example, as described above, the such non-ECG physiological sensors are configured to detect other types of patient physiological parameters and acoustic signals, such as tissue fluid levels, cardio-vibrations, lung vibrations, respiration vibrations, patient movement, etc.

In some examples, the therapy electrodes 1114 can also be configured to include sensors configured to detect ECG signals as well as other physiological signals of the patient. The connection pod 1130 can, in some examples, include a signal processor configured to amplify, filter, and digitize these cardiac signals prior to transmitting the cardiac signals to the medical device controller 1120. One or more of the therapy electrodes 1114 can be configured to deliver one or more therapeutic defibrillating shocks to the body of the patient 1102 when the medical device 1100 determines that such treatment is warranted based on the signals detected by the sensing electrodes 1112 and processed by the medical device controller 1120. Example therapy electrodes 1114 can include metal electrodes such as stainless-steel electrodes that include one or more conductive gel deployment devices configured to deliver conductive gel to the metal electrode prior to delivery of a therapeutic shock.

In some examples, the medical device 1100 can further include one or more motion sensors such as accelerometers 1162. As shown in FIG. 11A, in some examples an accelerometer 1162 can be integrated into one or more of a sensing electrode 1112, a therapy electrode 1114, the medical device controller 1120, and various other components of the medical device 1100.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 11B:
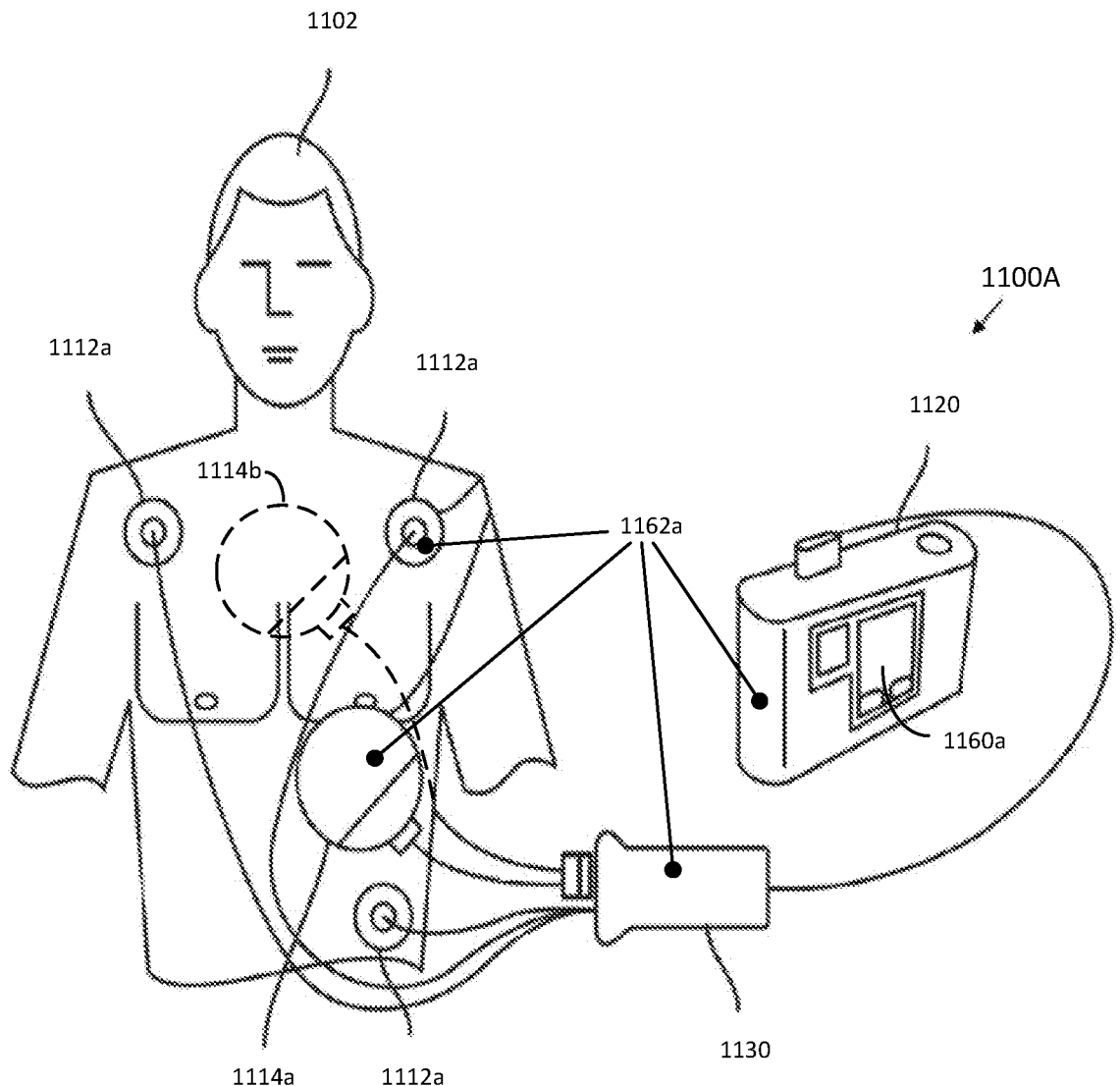

FIG. 11B illustrates a hospital wearable defibrillator 1100A that is external, ambulatory, and wearable by a patient 1102. Hospital wearable defibrillator 1100A can be configured in some implementations to provide pacing therapy, e.g., to treat bradycardia, tachycardia, and asystole conditions. The hospital wearable defibrillator 1100A can include one or more ECG sensing electrodes 1112a, one or more therapy electrodes 1114a and 1114b, a medical device controller 1120 and a connection pod 1130. For example, each of these components can be structured and function as like number components of the medical device 1100. For example, the electrodes 1112a, 1114a, 1114b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 1114a attaches to the front of the patient's torso to deliver pacing or defibrillating therapy. Similarly, the back adhesively attachable therapy electrode 1114b attaches to the back of the patient's torso. In an example scenario, at least three ECG adhesively attachable sensing electrodes 1112a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1160a can be configured to interact with a user other than the patient, e.g., a nurse, for device-related functions such as initial device baselining, setting and adjusting patient parameters, and changing the device batteries.

In some examples, the hospital wearable defibrillator 1100A can further include one or more motion sensors such as accelerometers 1162a. As shown in FIG. 11B, in some examples an accelerometer 1162a can be integrated into one or more of a sensing electrode 1112a (e.g., integrated into the same patch as the sensing electrode), a therapy electrode 1114a (e.g., integrated into the same patch as the therapy electrode), the medical device controller 1120, the connection pod 1130, and various other components of the hospital wearable defibrillator 1100A.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 11A.

Figure 11C:
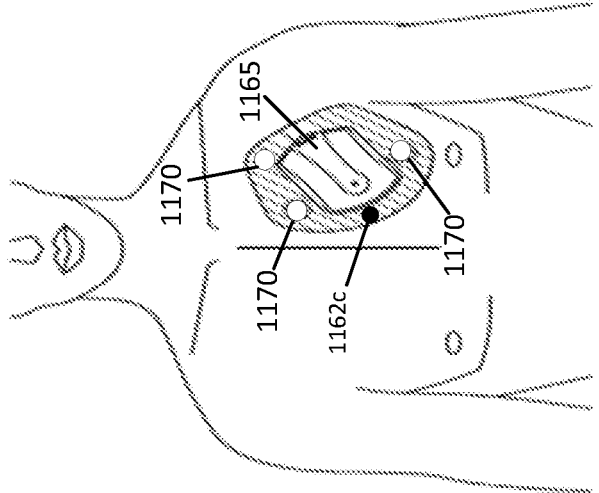
Figure 11C:
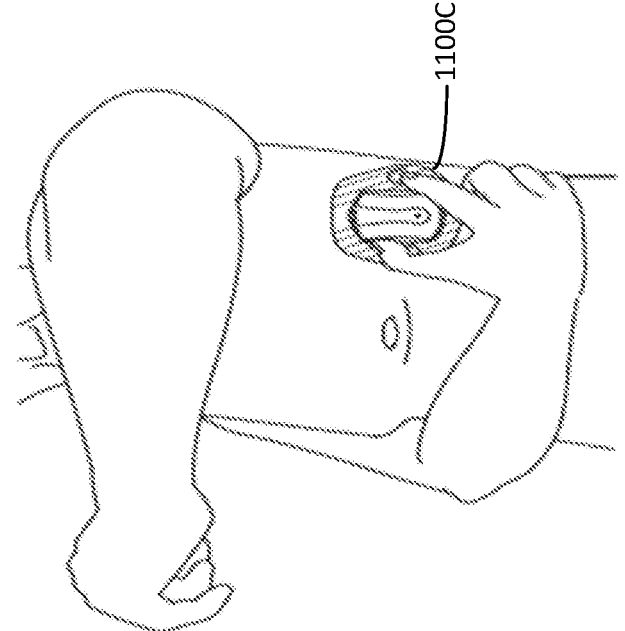
Figure 11D:
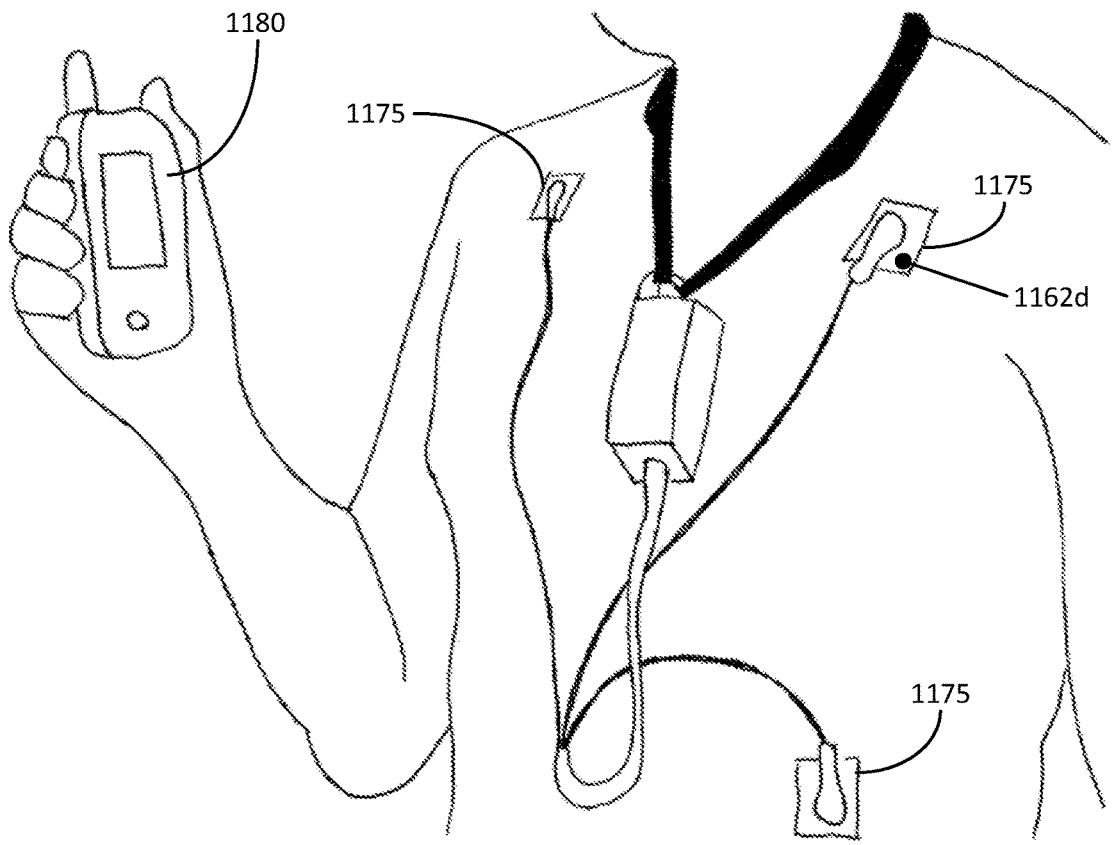

FIGS. 11C and 11D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 11C, an example wearable patient monitoring device 1100C can include tissue fluid monitors 1165 that use RF based techniques to assess fluid levels and accumulation in a patient's body tissue. Such tissue fluid monitors 1165 can be configured to measure fluid content in the lungs, typically for diagnosis and follow-up of pulmonary edema or lung congestion in heart failure patients. The tissue fluid monitors 1165 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1100C may be a cardiac monitoring device that also includes digital sensing electrodes 1170 for sensing ECG activity of the patient. Device 1100C can pre-process the ECG signals via one or more ECG processing and/or conditioning circuits such as an ADC, operational amplifiers, digital filters, signal amplifiers under control of a microprocessor. Device 1100C can transmit information descriptive of the ECG activity and/or tissue fluid levels via a network interface to a remote server for analysis. Additionally, in certain implementations, the device 1100C can include one or more accelerometers 1162c for measuring motion signals as described herein.

Referring to FIG. 11D, another example wearable cardiac monitoring device 1100D can be attached to a patient via at least three adhesive digital cardiac sensing electrodes 1175 disposed about the patient's torso. Additionally, in certain implementations, the device 1100D can include one or accelerometers 1162d integrated into, for example, one or more of the digital sensing electrodes for measuring motion signals as described herein.

Cardiac devices 1100C and 1100D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed cardiac monitoring for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 11A-11D) can communicate with a remote server via an intermediary or gateway device 1180 such as that shown in FIG. 11D. For instance, devices such as shown in FIGS. 11A-D can be configured to include a network interface communications capability as described herein in reference to, for example, FIG. 3.

Additionally, the devices described herein (e.g., FIGS. 11A-11D) can be configured to include one or more accelerometers as described herein. For example, as noted above in the discussion of FIGS. 1A and 1B, one or more sensors such as accelerometers, vibrational sensors, and RF sensors can be integrated into various components of a wearable device or included as standalone sensors configured to measure various signals for a patient.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A patient monitoring device configured to monitor cardiac activity and sleep stage information of a patient, the device comprising:
    a plurality of electrodes configured to be coupled externally to a patient to acquire electrocardiogram (ECG) signals from the patient and provide a therapeutic shock to the patient in response to detection of a cardiac arrhythmia, the patient monitoring device configured to provide for the detection of the cardiac arrhythmia based on one or more cardiac arrhythmia detection parameters;
    at least one motion sensor configured to generate at least one motion signal based upon movement of the patient;
    a cardio-vibrational sensor configured to generate a cardio-vibrational signal of the patient; and
    at least one processor operably coupled to the plurality of electrodes and the at least one motion sensor, the at least one processor configured to
        receive the at least one motion signal from the at least one motion sensor and derive one or more motion parameters from the at least one motion signal,
        receive the ECG signals from the plurality of electrodes and derive one or more ECG parameters from the ECG signals, the one or more ECG parameters comprising at least one heart rate parameter,
        determine whether the patient is in an immobilized sleep stage or a non-immobilized sleep stage based upon analysis of the one or more motion parameters and the one or more ECG parameters comprising the at least one heart rate parameter,
        adjust the one or more cardiac arrhythmia detection parameters such that the patient monitoring device operates in a first monitoring and treatment mode when the at least one processor determines that the patient is in the immobilized sleep stage,
        commence monitoring the cardio-vibrational signal of the patient when the at least one processor determines that the patient is in the immobilized sleep stage, wherein monitoring the cardio-vibrational signal of the patient includes determining one or more electromechanical parameters of a heart of the patient using the cardio-vibrational signal, and
        monitor the patient for the cardiac arrhythmia using the first monitoring and treatment mode.

2. The patient monitoring device of claim 1, wherein the at least one processor is configured to determine whether the patient is in the immobilized sleep stage by being configured to:
    monitor the ECG signals to determine whether heart rate deviation from a baseline resting heart rate for the patient exceeds a deviation threshold over a period of time;
    analyze the one or more motion parameters over the period of time; and
    determine if the patient is in the immobilized sleep stage based upon the heart rate deviation and analysis of the one or more motion parameters over the period of time.

3. The patient monitoring device of claim 2, wherein one or both of:
    the deviation threshold comprises one or more of greater than 1% deviation from the baseline resting heart rate, greater than 2% deviation from the baseline resting heart rate, or greater than 5% deviation from the baseline resting heart rate; and
    the period of time comprises one or more of five minutes, seven minutes, ten minutes, thirty minutes, forty-five minutes, or one hour.

4. The patient monitoring device of claim 2, wherein the at least one processor is configured to:
    adjust the one or more cardiac arrhythmia detection parameters such that the patient monitoring device operates in a second monitoring and treatment mode; and
    monitor the patient for the cardiac arrhythmia using the second monitoring and treatment mode.

5. The patient monitoring device of claim 4, wherein the at least one processor is further configured to:

monitor the patient using the second monitoring and treatment mode;

determine whether the patient has transitioned from the non-immobilized sleep stage to the immobilized sleep stage; and monitor the patient using the first monitoring and treatment mode when the at least one processor determines that the patient has transitioned from the non-immobilized sleep stage to the immobilized sleep stage.

6. The patient monitoring device of claim 1, wherein the at least one processor is configured to commence monitoring a radiofrequency-based physiological signal when the at least one processor determines that the patient is in the immobilized sleep stage.

7. The patient monitoring device of claim 6, wherein the patient monitoring device further comprises:

a radiofrequency sensor, wherein the at least one processor is configured to determine one or more of heart wall movement information or thoracic fluid level information from the radiofrequency-based physiological signal.

8. The patient monitoring device of claim 1, wherein the at least one processor is configured to adjust one or more treatment parameters when the at least one processor determines that the patient is in the immobilized sleep stage; and wherein the one or more treatment parameters comprise one or more of a pacing pulse rate, a high-energy pacing pulse energy level, a low-energy pacing pulse energy level, a defibrillation shock energy level, or defibrillation shock timing information.

9. The patient monitoring device of claim 1, wherein the at least one processor is configured to adjust one or more alarm parameters when the at least one processor determines that the patient is in the immobilized sleep stage; and wherein the one or more alarm parameters comprises one or more of alarm type, alarm volume, alarm duration, or patient response time information.

10. The patient monitoring device of claim 1, wherein the immobilized sleep stage comprises one or more of an N3 sleep stage, an N4 sleep stage, or REM sleep stage, and the non-immobilized sleep stage comprises one or more of consciousness, an N1 sleep stage, or an N2 sleep stage.

11. The patient monitoring device of claim 1, wherein the one or more motion parameters comprises one or more of patient respiration information, patient physical movement information, patient body position information, or a rotational motion parameter that quantifies rotational motion of the patient as measured by the at least one motion sensor.

12. The patient monitoring device of claim 1, wherein the at least one processor is further configured to derive one or more additional motion parameters from one or more impedance-based measurements from the plurality of electrodes; and wherein the at least one processor is configured to determine whether the patient is in the immobilized sleep stage or the non-immobilized sleep stage further based on the one or more additional motion parameters.

13. The patient monitoring device of claim 1, wherein the one or more ECG parameters comprise one or more of heart rate, heart rate variability, premature ventricular contraction, premature ventricular contraction burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave *alternans*, T wave variability, or ST segment changes, and the one or more cardiac arrhythmia detection parameters comprise one or more of a ventricular tachycardia onset heart rate, a ventricular fibrillation onset heart rate, a bradycardia onset heart rate, a tachycardia onset heart rate, or an asystole onset threshold.

14. The patient monitoring device of claim 1, wherein the at least one processor is further configured to adjust one or more of a cardiac arrhythmia detection confidence level or a noise threshold when the at least one processor determines that the patient is in the immobilized sleep stage, wherein the cardiac arrhythmia detection confidence level is used by the at least one processor in one or both of identification of the cardiac arrhythmia or verification of treatment of the cardiac arrhythmia, and wherein the noise threshold defines a level of noise in the ECG signals within which derivation of the one or more ECG parameters is permitted to occur.

15. The patient monitoring device of claim 1, wherein the at least one processor is further configured to:

monitor a heart rate of the patient when the at least one processor determines that the patient is in the immobilized sleep stage to derive patient heart rate information;

compare the patient heart rate information and a baseline resting heart rate for the patient; and adjust and/or verify the baseline resting heart rate based upon comparing of the patient heart rate information and the baseline resting heart rate to determine an updated baseline resting heart rate for the patient.

16. The patient monitoring device of claim 1, wherein the at least one processor is further configured to, when the at least one processor determines that the patient is in the immobilized sleep stage:

determine at least one occurrence of a premature ventricular contraction (PVC) from the ECG signals;

upon occurrence of the PVC, monitor changes in the ECG signals to measure a cardiac response of the heart of the patient following the PVC;

determine a heart rate turbulence value for the patient based upon the monitored changes in the ECG signals; and store the heart rate turbulence value on a computer-readable medium operably coupled to the at least one processor for analysis.

* * * * *